United States Patent
Ma et al.

(10) Patent No.: US 10,919,849 B2
(45) Date of Patent: Feb. 16, 2021

(54) ONLINE CONTINUOUS FLOW PROCESS FOR THE PREPARATION OF ORGANIC PEROXIDES DIRECT FROM ALCOHOLS OR ALKANES

(71) Applicant: Shanghai Hybrid-chem Technologies, Shanghai (CN)

(72) Inventors: Bing Ma, Shanghai (CN); Shuai Pan, Shanghai (CN); Xinlin Shu, Shanghai (CN)

(73) Assignee: SHANGHAI HYBRID-CHEM TECHNOLOGIES, Shanghai (CN)

( * ) Notice: Subject to any disclaimer, the term of this patent is extended or adjusted under 35 U.S.C. 154(b) by 0 days.

(21) Appl. No.: 16/787,029

(22) Filed: Feb. 11, 2020

(65) Prior Publication Data

US 2020/0199068 A1 Jun. 25, 2020

Related U.S. Application Data

(63) Continuation of application No. PCT/CN2018/100115, filed on Aug. 10, 2018.

(30) Foreign Application Priority Data

| Aug. 12, 2017 | (CN) | .......................... | 2017 1 0688671 |
| Aug. 6, 2018 | (CN) | .......................... | 2018 1 0887206 |
| Aug. 9, 2018 | (CN) | .......................... | 2018 1 0900615 |

(51) Int. Cl.
| *C07C 407/00* | (2006.01) |
| *C07C 409/02* | (2006.01) |
| *B01J 19/00* | (2006.01) |
| *C07C 409/22* | (2006.01) |
| *C07C 409/32* | (2006.01) |
| *C07C 409/38* | (2006.01) |

(52) U.S. Cl.
CPC ....... *C07C 407/003* (2013.01); *B01J 19/0006* (2013.01); *B01J 2219/00033* (2013.01); *C07C 409/02* (2013.01); *C07C 409/22* (2013.01); *C07C 409/32* (2013.01); *C07C 409/38* (2013.01)

(58) Field of Classification Search
CPC ... C07C 407/00; C07C 407/03; C07C 409/02; C07C 409/22; C07C 409/32; C07C 409/38
See application file for complete search history.

(56) References Cited

FOREIGN PATENT DOCUMENTS

| CN | 101287704 A | 10/2008 |
| CN | 102558399 B | 7/2012 |
| CN | 102617432 A | 8/2012 |
| CN | 101479239 B | 5/2013 |
| CN | 104592080 A | 5/2015 |
| CN | 102336694 B | 9/2015 |
| CN | 106588734 A | 4/2017 |
| WO | WO2017072190 A1 | 5/2017 |

OTHER PUBLICATIONS

ISR corresponding to PCT/CN2018/100115 , dated Oct. 31, 2018.

*Primary Examiner* — Sikarl A Witherspoon

(57) ABSTRACT

A continuous flow production process for preparing organic peroxides directly from alcohols or alkanes takes very safe alcohols or alkanes as starting materials, and directly reacts to obtain designated peroxides. The production process is carried out in an integrated continuous flow reactor, and a safe starting source of alcohol or alkane is continuously added at the feed inlet of the integrated continuous flow reactor, and continuously provided with a designated peroxide at the discharge port of the integrated continuous flow reactor.

23 Claims, 1 Drawing Sheet

ONLINE CONTINUOUS FLOW PROCESS FOR THE PREPARATION OF ORGANIC PEROXIDES DIRECT FROM ALCOHOLS OR ALKANES

CROSS REFERENCE TO RELATED APPLICATIONS

This application is a continuation of PCT Patent Application No. PCT/CN2018/100115, filed on Aug. 10, 2018, entitled "Online Continuous Flow Process for the Preparation of Organic Peroxides Direct from Alcohols or Alkanes," which claims foreign priority of China Patent Application Nos. 201710688671.5, filed Aug. 12, 2017, 201810887206.9, filed Aug. 6, 2018, and 201810900615.8, filed Aug. 9, 2018 in the China National Intellectual Property Administration, the entire contents of which are hereby incorporated by reference in their entireties.

FIELD OF THE DISCLOSURE

The disclosure relates to the field of chemistry, in particular to an online continuous flow process for the preparation of organic peroxides direct from alcohols or alkanes; the organic peroxides are flammable and explosive compounds.

BACKGROUND OF THE DISCLOSURE

Organic peroxide is an organic compound containing —O—O— peroxyl functional group formed by the replacement of hydrogen atoms in hydrogen peroxide by alkyl, acyl, aromatic and other organic groups. It is characterized by the decomposition of oxygen-containing radicals when heated over a certain temperature, which is unstable and easy to decompose. Organic peroxides produced in chemical industry are mainly used as polymerization initiators and catalysts of synthetic resins. In the field of polymer materials, organic peroxides are used as initiators of free radical polymerization and grafting reaction, crosslinking agents of rubber and plastic, curing agents of unsaturated polyester and molecular weight and molecular weight distribution regulators in the preparation of spinning-grade polypropylene. Organic peroxides are the sources of free radicals used in the following applications: 1. initiator for free radical polymerization and copolymerization of vinyl and diene monomers; 2. vulcanizer for thermosetting resin; 3. crosslinker for elastomer and polyethylene.

In addition to the above polymer material industry, organic peroxides, as photoinitiators and sensitizers, are used in film industry, photosensitive polymer materials, photosensitive resins, etc., and are also commonly used in the production of epoxy resin; in medical materials, the initiators composed of organic peroxides and drugs are used in the synthesis of slow-release drug delivery matrix (such as microspheres, pellets, film); in organic synthesis, organic peroxides are mainly used as oxidants and epoxidators. In addition, organic peroxides are also used in disinfection of medical equipment and food, bleaching agent, decolorizing agent, bactericide, cleaning agent, etc. in daily chemical industry such as textiles and paper.

Peroxycarboxylates and peroxycarbamates are important organic peroxides, such as tert-butyl peroxy 2-ethylhexyl carbonate, isopropyl peroxyneodecanoate and 1,1,3,3-tetramethyl peroxyneodecanoate. Peroxycarboxylate and peroxycarbamate are low-temperature initiators of free radical polymerization, which are widely used in the production fields of polyethylene (LDPE), polyvinyl chloride (PVC), polystyrene (PS), styrene copolymer (such as ABS), polymethylacrylate (PMMA) and polyvinyl acetate (PVAc). At the same time, it is also a high-temperature curing agent of unsaturated polyester. However, ketal peroxide is mainly used as crosslinker of unsaturated polyester, initiator of rubber and plastic. At present, the market at home and abroad has a growing demand for peroxycarboxylate, peroxycarbamate and peroxyketal, so the development of continuous production process of organic peroxides has practical significance and great prospect.

Organic peroxides are very active compounds, which are easy to decompose into free radicals and oxygen with high reactivity. In this process, a lot of heat will be released and even explode. As an organic peroxide, its important feature is the self-accelerating decomposition temperature (SADT). When equal to or higher than the SADT, the heat release rate of the decomposition reaction of organic peroxide is out of balance with the environmental heat dissipation rate, that is, the heat of the system is accumulating continuously. At this time, the organic peroxide can cause dangerous self-accelerating decomposition reaction through thermal decomposition and explosion or fire in adverse environment. Contact with incompatible materials and increased mechanical stress can lead to decomposition at or below SADT.

The decomposition of organic peroxides occurs under the effect of temperature, which is due to the existence of oxygen-oxygen bonds that can be opened in the energy range $\Delta H$ of about 84 to 184 kj/mol, and the energy range depends on the properties of the organic peroxides. That is to say, the energy required for the decomposition of different organic peroxides to open the oxygen-oxygen bond is different according to their respective properties. Therefore, the SADT and thermal stability of different organic peroxides are quite different. For example, the SADT of cumyl peroxy neodecanoate (CNP) is 10° C., corresponding to the half-life of 10 hours is 38° C.; the SADT of tert-butyl peroxypivalate (TBPV) is 20° C., corresponding to the half-life of 10 hours is 57° C.; the SADT of tert-butyl peroxy neodecanoate is 15° C., corresponding to the half-life of 10 hours is 46° C.; the SADT of tert-butylperoxyl-2-ethylhexyl carbonate (TBEC) is 60° C., corresponding to the half-life of 10 hours is 100° C.; the SADT of 1,1-di(tert-butylperoxyl) cyclohexane is 70° C., corresponding to the half-life of 10 hours is 94° C. At the same time, due to the difference of structure, the synthesis routes and raw materials of different organic peroxides are different, and the physical and chemical properties of raw materials are also different. These differences lead to the absence of a so-called "universal" process that can be applied to all organic peroxides, making it difficult for different production processes of organic peroxides to transplant and apply each other. The production of each specific organic peroxide needs to specially design and develop personalized and applicable process, conditions and parameters according to its self-accelerating decomposition temperature and thermal stability, as well as the physical and chemical properties of raw materials.

The preparation of peroxide carboxylate, peroxide carbamate or peroxide ketal by the prior art includes the following two steps:

The first step is oxidation reaction. Alcohols or alkanes react with oxidants to synthesize alkylperoxides $R(OOH)n$ and dialkylperoxides $ROOR$. After separation and purification, impurities such as dialkyperoxides $ROOR$ and water are removed to obtain the product of oxidation reaction, alkylperoxides $R(OOH)n$. The general reaction formula is as follows:

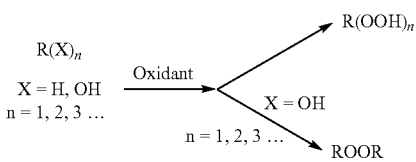

The second step is condensation reaction. Alkylperoxide R(OOH)n reacts with alkali and acyl compounds to synthesize peroxycarboxylate or peroxycarbamate. The general reaction formula is as follows:

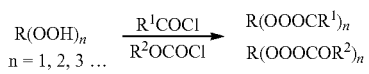

The alkoxyperoxide R(OOH)n reacts with acid and alcohol or ketone to synthesize peroxyketal. The general reaction formula is as follows:

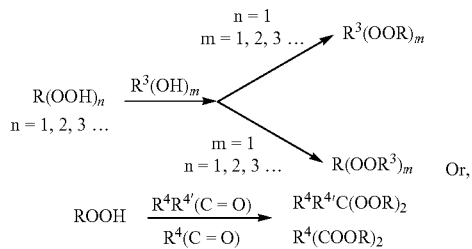

wherein, R is selected from saturated or unsaturated $C_1$-$C_{12}$ alkyl, unsubstituted or substituted aryl, unsubstituted or substituted heterocycloaryl, unsubstituted or substituted saturated heterocycloalkyl, unsubstituted or substituted partially saturated heterocycloalkyl, unsubstituted or substituted cycloalkyl.

$R^1$ is selected from saturated or unsaturated $C_1$-$C_{20}$ alkyl, unsubstituted or substituted aryl, unsubstituted or substituted heterocyclic aryl.

$R^2$ is selected from saturated or unsaturated $C_1$-$C_{20}$ alkyl group, unsubstituted or substituted aryl group, unsubstituted or substituted heterocycloaryl group, unsubstituted or substituted saturated heterocycloalkyl group, unsubstituted or substituted partially substituted heterocycloalkyl group, unsubstituted or substituted cycloalkyl group.

$R^3$ is selected from saturated or unsaturated $C_1$-$C_{12}$ alkyl group, unsubstituted or substituted aryl group, unsubstituted or substituted heterocycloaryl group, unsubstituted or substituted saturated heterocycloalkyl group, unsubstituted or substituted partially substituted heterocycloalkyl group, unsubstituted or substituted cycloalkyl group.

$R^4$ or $R^{4'}$ are selected from saturated or unsaturated $C_1$-$C_{12}$ alkyl, unsubstituted or substituted aryl, unsubstituted or substituted heterocycloaryl, unsubstituted or substituted saturated heterocycloalkyl, unsubstituted or substituted partially saturated heterocycloalkyl, unsubstituted or substituted cycloalkyl.

The improvement of industrial production process of chemical products mainly refers to the improvement of process. The said process refers to the method and process of processing or reacting raw materials with various equipment to obtain the final product. It is a process of obtaining the product by adjusting the technical parameters such as temperature, pressure, material ratio, etc. of the chemical reaction or physical process in combination with the equipment. That is to say, the production process refers to the process of realizing the chemical reaction or physical process in the industrial scale. The relationship between production process and reaction is not one-to-one. A process can contain one reaction or multiple reactions. The reaction and the corresponding reaction route involved in the preparation of chemical products are determined by their reaction mechanism, but for the same reaction route, it can be realized by different production processes. The possible effects of production process optimization and improvement are: first, improve production efficiency, increase production capacity and reduce production cost; second, improve process safety; third, improve product quality; fourth, reduce "three wastes" emissions.

In the process of industrial production of peroxycarboxylate, peroxycarbamate or peroxyketal, the oxidation reaction and condensation reaction correspond to the oxidation process and condensation process, respectively. The oxidation reaction and condensation reaction are both oil-water two-phase reactions, with low reaction efficiency and a large amount of water in the reaction system. The oxidant used in the first step of oxidation reaction is liquid oxidant (e.g. hydrogen peroxide) or gas oxidant (e.g. oxygen). The two problems caused by oxidation reaction are: 1) due to the limitation of oxidation process, the oxidant will not be completely converted, and will inevitably generate dialkyl peroxide. Dialkyl peroxide and oxidant without complete reaction will become the impurities oxidation, what must be removed before the next condensation reaction. For example, when hydrogen peroxide is used as oxidant, peroxide impurities (dialkylperoxides and hydrogen peroxide) will directly affect the quality of the final product (peroxycarboxylate, peroxycarbamate, peroxyketal). Because different organic peroxides have different self-accelerating decomposition temperature and half-life, the use of organic peroxides is to use these different self-accelerating decomposition temperature and half-life characteristics, so organic peroxides cannot be mixed in general, especially the organic peroxides with great difference in self accelerating decomposition temperature and half-life, or it will seriously affect the use effect. For example, the target product is tert-butyl peroxyneodecanoate. The SADT of tert-butyl peroxyneodecanoate is 15° C., the corresponding temperature of 10 h half-life is 46° C.; the SADT of Di tert-butyl hydrogen peroxide generated in the process of preparing tert-butyl peroxyneodecanoate is 80° C., the corresponding temperature of 10 h half-life is 121° C. The SADT and half-life of different concentrations of hydrogen peroxide are different. At room temperature (usually 25° C.), the half-life of hydrogen peroxide in fresh water is 8 hours to 20 days. It can be seen that the SADT and half-life of the three are very different, and the mixture of the three cannot meet the single use demand. Therefore, in the synthesis process of tert-butyl peroxyneodecanoate, the dialkyl peroxide and hydrogen peroxide must be removed after the oxidation reaction; otherwise, the quality and performance of tert-butyl peroxyneodecanoate will be seriously affected. 2) A large number of water and impurities will affect the condensation reaction concentration, and then affect the reaction rate, resulting in a greatly reduced production efficiency. When oxygen is used as oxidant, the main impurities are sodium carbonate, initiator and water, which also have the above two problems. First, the initiator is usually free radical initiator such as azodiisobutycyanogen (SADT is 50° C., 10 h half-life decomposition temperature is 65° C.), diisopropylbenzene peroxide (SADT is 75° C., 10 h half-life decomposition temperature is 117° C.), etc. If they are not removed and mixed into final product, they will also affect the quality and performance of the product. Second, impurities such as water will affect the reaction rate and further affect the production efficiency. For example, it is mentioned in the literature that 500 g diisopropylbenzene, 200 g water, 20 g $Na_2CO_3$ and 6 g azodiisobutyrcyanide are added to the autoclave for 60 h to synthesize diisopropylbenzene dihydroperoxide. Only when the water phase is still, can the upper oil phase be separated to carry out the next reaction (New crosslinker di tert-butyl Study on the synthesis of diisopropylperoxide, chemical world, 2008 (1): 38-41).

In the existing production process of synthesizing peroxycarboxylate, peroxycarbamate or peroxyketal, the product obtained from the oxidation process is a mixture containing alkyl peroxide, impurities and a large amount of water. In order to ensure the effective condensation process, the impurities and a large amount of water in the mixture need to be removed through the purification process to produce an alkyl peroxide that meets the standards of commercial industrial products (for example, the requirements for commercial tert-butyl hydroperoxides are as follows: di tert-butyl hydroperoxides ≤0.08%, tert-butanol ≤0.5%, and other organics ≤0.4%). The purification process can be gas-liquid separation, acid-base method, vacuum distillation or distillation, flash separation, etc., and the purification process usually adopts intermittent process. The purification steps of cumene hydrogen peroxide mentioned in Chinese Patent CN106588734 include gas-liquid separation, flash separation and concentration. The synthesis of tert-butyl hydrogen peroxide mentioned in Chinese Patent CN102617432 is followed by static stratification to obtain the upper organic phase. Add alkali to organic phase with the reaction temperature 10 to 50° C. and the reaction time 0.5 to 4 h. The upper organic phase is removed, and the lower water phase reacts with chloroester to obtain tert-butyl peroxy 2-ethylhexylcarbonate. It can be seen that different purification processes are required for the preparation of different alkyl peroxides, and separate equipment such as distillation tower is also required, and most of the equipment required are different. There is no general equipment and process available to purify various alkyl peroxides.

At the same time, after the existing purification process, only the crude peroxycarboxylate, peroxycarbamate or peroxyketal is obtained, which contains water, alkyl peroxide, salt, etc., and after the workup process, the products that meet the market standard can be obtained (for example, the requirements of the market for tert-butyl peroxyneodecanoate are as follows: chloride ion content ≤0.05%, tert-butyl hydrogen peroxide content ≤0.1%). The workup process can be separation, alkali washing, water washing, vacuum distillation or distillation, flash separation, drying, etc. The workup method of tert-butyl peroxyneodecanoate disclosed in Chinese Patent CN102558399 is to stand for 20 to 40 min after the reaction, separate the mother liquor, wash the reaction product to pH 5 to 7, add alkane solvent and stir for 20 to 30 min to obtain solvent-type peroxyneodecanoate; the workup time of butyl product is more than 40 min. The workup method of 1,1-di(tert-butyl peroxide) cyclohexane disclosed in Chinese patent CN102336694 is to wash the mother liquor with alkali and water to get the neutral reaction solution, and the colorless liquid obtained by vacuum distillation is the product 1,1-di(tert-butyl peroxide) cyclohexane; the conventional time of reference to the existing workup process is 1 to 2 hours. The existing workup process takes a long time and has low efficiency. At the same time, separate equipment such as distillation tower is needed. The workup processes of different peroxycarboxylate, peroxycarbamate or peroxyketal are also different. There is no general equipment and process in the existing production process that can purify various peroxycarboxylate, peroxycarbamate or peroxyketal.

Therefore, the production of peroxycarboxylate, peroxycarbamate or peroxyketal that meet the market standard by the existing process needs to be divided into four steps. The first step is the oxidation process, and the product is a mixture containing alkyl peroxide, impurities and a large amount of water; the second step is the pure chemical process, in which impurities and a large amount of water are removed to produce the alkyl peroxide that meets the market industrial product requirements (i.e. Intermediate products) and store them for standby; the third step is the condensation process to prepare the target product (peroxycarboxylate, peroxycarbamate or peroxyketal); the fourth step is the workup process to remove impurities and water to prepare the peroxycarboxylate, peroxycarbamate or peroxyketal that meet the requirements of commercial industrial products. In the existing production process, a certain amount of alkyl peroxides must be accumulated after the oxidation process, that is, there is the accumulation and storage of intermediate products on the macro-level; the alkyl peroxides can only be used in the next condensation process after purification, that is, there is the purification process of intermediate products and related operation process in the process. This shows that the oxidation process and condensation process are essentially two independent processes. Therefore, the preparation of peroxycarboxylate, peroxycarbamate or peroxyketal by the existing process is a batch process as a whole. In addition, the said alkyl peroxide belongs to inflammable and explosive dangerous chemicals, so there is a great safety risk in the process of accumulation, storage and purification of such compounds, and because the said alkyl peroxide is extremely sensitive to temperature, it needs cold chain storage and transportation, which greatly increases the use and production cost. There are accumulation, storage and purification of alkyl peroxides in the prior art, so it is impossible to seamlessly connect the oxidation process and condensation process, so as to directly prepare peroxycarboxylate, peroxycarbamate and peroxyketal from alcohol or alkane; at the same time, since there is no general workup equipment and process in the prior art, it is impossible to combine the oxidation, condensation process and workup process. In order to achieve full continuity, a certain amount of peroxycarboxylate, peroxycarbamate or peroxyketal is required to be stored, and the said peroxycarboxylate, peroxycarbamate or peroxyketal are inflammable and explosive dangerous chemicals, so there is a great safety risk in the storage and workup of such compounds, and because of the said peroxycarboxylate and carbon peroxide acid ester or peroxidized ketal is extremely sensitive to temperature, so it needs cold-chain storage and transportation, which further increases the cost of use and production.

The general formula of the alkyl peroxide is R(OOH)n. R is selected from saturated or unsaturated $C_1$-$C_{12}$ alkyl, unsubstituted or substituted aryl, unsubstituted or substituted heterocycloaryl, unsubstituted or substituted saturated heterocycloalkyl, unsubstituted or substituted partially saturated heterocycloalkyl, unsubstituted or substituted cycloalkyl.

Furthermore, R is selected from saturated or unsaturated $C_3$-$C_8$ alkyl, unsubstituted or substituted aryl, unsubstituted or substituted heterocycloaryl, unsubstituted or substituted saturated heterocycloalkyl, unsubstituted or substituted partially saturated heterocycloalkyl, unsubstituted or substituted cycloalkyl.

Furthermore, R is selected from tert-butyl, tert-, isopropylphenyl, 1,4-diisopropyl, 2,4,4-trimethyl-2-amyl, 2,5-dimethylhexyl.

Furthermore, alkyl peroxides are selected from:
tert-butyl hydroperoxides CAS No.: 75-91-2, tert-amyl hydroperoxides CAS No.: 3425-61-4, CAS No.: 4212-43-5, 1, 1, 3, 3-tetramethyl-butyl hydroperoxides CAS No.: 5809-08-5, cumene hydroperoxides CAS No.: 80-15-9, 2, 5-dimethyl-2, 5-bis(hydroperoxides) hexane CAS No.: 3025-88-5, dihydroxy-1, 4-diisopropylbenzene CAS No.: 3159-98-6.

There are two most important characteristics of batch process. One is that there is "stand" or "interruption" in the process. The other is that the product production is separate, that is, there are batches of products and only a fixed number of products can be produced in a batch. That is to say, for each batch of production, a fixed number of raw materials react according to the order of reaction steps, and finally a limited fixed number of products are obtained; then a fixed number of raw materials are put in, and the next batch of reaction is carried out according to the same steps, and a limited fixed product is produced.

There are two ways to realize the batch process: 1) using multiple reactors (for example, flasks, reactors, etc.) to realize each step of reaction in one reactor; 2) using a reactor (for example, flasks, reactors, etc.) to realize each step of reaction in turn, adding multiple raw materials according to the reaction process, that is after one-step reaction, there will be "stand" waiting for further addition of raw materials for subsequent reaction. Some literatures also call mode 2) as continuous, which is also intermittent in nature, because there is "stand" in the process, and it needs to wait for feeding, or it needs to adjust to the appropriate temperature for the next reaction (such as temperature rise, temperature drop or heat preservation).

The main problems of batch process are as follows:
1. The batch operation efficiency is not high, and the reaction time is very long. In the process, there must be oxidation products (i.e. intermediate products) alkyl peroxides. In addition, a large number of oxidation products and final products need to be stored and transported in cold chain, resulting in high product use and production cost for a long time.

2. In the first step of oxidation process, whether oxygen self-oxidation or hydrogen peroxide oxidation is used, the liquid holding capacity of batch process reactor is large, and a large amount of pure oxygen or hydrogen peroxide is required for a single reaction, so there is a great potential safety hazard in the batch process.

3. The third step of condensation process is exothermic reaction, which requires the reactor to have good heat exchange performance to ensure the temperature does not runaway. Once the temperature is too high, the product will decompose, and the yield will be reduced. The existing batch process mainly realizes the control of reaction temperature by controlling the adding speed of oxidant (slow dropping or slow ventilation) combined with the corresponding heat transfer device. In this way, the operation time is greatly prolonged, and the production efficiency is reduced; in addition, because a large number of peroxides exist for a long time, the process safety risks are great, and the process safety problems are not fundamentally solved. That is to say, the safety, product yield and quality stability of batch process need to be improved.

4. The batch process will inevitably bring scaling up effect, which will greatly hinder the scale-up of industrial production. The amplification effect refers to the research results of chemical process (i.e. small-scale) experiments (e.g. laboratory scale) with small equipment, which are often quite different from the results of large-scale production devices (e.g. industrial scale) under the same operating conditions. The effect of these differences is called amplification. The main reason is that the distribution of temperature, concentration and residence time in small-scale experimental equipment is different from that in large-scale equipment. In other words, under the same operating conditions, it is impossible to completely repeat the research results of small-scale experiments on the scale of industrialization; if we want to get the same or similar results with small-scale experiments on the scale of industrialization, we need to change the process parameters and operating conditions through optimization and adjustment. For chemical process, amplification effect is a difficult and urgent problem. If it is not solved, it will lead to great uncertainty in the production process and product quality. First, it will directly cause the quality of downstream products to be unstable and difficult to control. Second, it will cause the process parameters of the production process to fluctuate, which will lead to the inability to effectively control the production process, so that the production safety cannot be guaranteed, and many potential safety hazards are buried for the production process.

Chinese patent CN101479239 discloses a method for continuous preparation of organic peroxides by using a plate heat exchanger with high heat exchange capacity. The selected peroxides are continuously prepared at a given temperature by introducing different reactants at different positions (plates) of the plate heat exchanger. The given temperature is the temperature above which organic peroxides become heat sensitive. The results show that the reaction temperature is lower than SDAT, and the optimal reaction temperature range is 5 to 60° C. Compared with batch process, the yield is close. Although the temperature is higher but lower than SADT. The synthetic reaction time is in the range of 1-45 seconds in laboratory scale, and up to 2-3 minutes in industrial scale. The reaction time refers to the time required for the reaction material to enter the reactor until the end of the reaction to obtain the crude product of the target product, excluding the time for workup. Compared with the batch process, the continuous preparation method has certain advantages in production efficiency and safety. However, due to the inevitable amplification effect, the industrial scale reaction time is 2-180 times of the laboratory scale, and there is a large uncertainty (the extension of reaction time by 2-180 times in a very wide range), which greatly increases the difficulty of industrialization. This kind of amplification effect with large uncertainty will bring many disadvantages to the industrial application of the process. For example, when the process is expanded to the industrial scale, it can only take multiple step-by-step amplification methods. In order to obtain the results consistent with the scale of the laboratory, each amplification process needs to adjust and optimize the process conditions and parameters, which will greatly consume human resources and project development time. Even if multiple successive amplification is used, the amplification effect may not reach the good result of the scale of the laboratory due to its large variation; meanwhile, the large-scale uncertain amplification effect will affect the stability and reliability of the process, resulting in unstable product quality and difficult to control; in addition, it will also bring potential safety risks to the production process. At the same time, the patent only reports the continuous process of alcohol or alkane to produce alkyl peroxide or the continuous process of alcohols or alkanes to produce alkyl peroxidesalkyl peroxide or alkyl peroxidesalkyl peroxide to produce peroxyester, but it cannot realize the continuous direct production of peroxycarboxylate, peroxycarbamate and peroxyketal with alcohol or alkane as the starting material.

Chinese patent CN102617432 discloses the method of producing tert-butyl peroxy-2-ethylhexyl carbonate from tert-butyl alcohol, but the problems of the patent are as follows:

First, there are still a large number of processes in the production process for quite a period of time, such as accumulation, purification and retention of oxidation product tert-butyl hydrogen peroxide. As mentioned above, this brings a great potential safety hazard, and in order to ensure the production safety, these processes need to maintain at low temperature, which greatly increases the production cost.

Second, the whole process from tert-butyl alcohol to tert-butyl peroxy-2-ethylhexyl carbonate is batch process, so there must be amplification effect in industrial scale-up, which greatly increases the difficulty of industrial scale-up.

Third, the production time is 3-18 hours. The reaction time is long and the production efficiency is low. It is impossible to realize online production and produce-to-use.

To sum up, there are many problems in the existing production process of organic peroxides: the accumulation, purification, storage and transportation process of organic peroxides (including oxidation reaction products and products) still exists for quite a period of time; the process has a great potential safety hazard; the continuous flow process of peroxycarboxylates, peroxycarbamates or peroxyketals directly from alcohols or alkanes is not yet possible and plug-and-produce system matched with it cannot achieve. Thus, the real online production of the above organic peroxides cannot be realized. All of these make it impossible to fundamentally solve the huge safety risks in the production and use of organic peroxides and reduce the production and use costs. In addition, there are amplification effects in different degrees in the existing processes, resulting in a large amount of human and material resources consumed and many uncertainties in the process of industrial scale-up; there are also problems in the reliability of the process after scale-up, resulting in unstable product quality and difficult to control; and the production process lacks flexibility and has potential safety risks. Due to the low reaction temperature, the total reaction time is too long and the production efficiency is reduced, which increase the difficulty of industrialization. If it cannot realize mass production, it limits the application. Therefore, it is necessary to find a continuous production process of organic peroxides which is easy to operate, safe, efficient, online production, mass production and without amplification effect.

SUMMARY OF THE DISCLOSURE

In view of the shortcomings of existing processes, the technical problem to be solved in this disclosure is to provide an online continuous flow process for the preparation of organic peroxides direct from alcohols or alkanes. The organic peroxides refer to peroxycarboxylates, peroxycarbamates or peroxyketals. The production process directly produces high-risk organic peroxides from safe starting materials (alcohols or alkanes). There is no process of accumulation, purification and residence of dangerous alkyl peroxides (i.e. intermediate products) macroscopically, realizing the produce-to-use of organic peroxides, in addition, it overcomes the problem of amplification effect and realizes online manufacturing. The production and use of the organic peroxide products are carried out at the same time, which is seamlessly linked with the downstream process and synchronously linked, so as to realize the flexible manufacturing of produce-to-use and ready-to-use. The process is simple, safe and efficient, without amplification effect. The yield and content of the organic peroxide products are high. It is easy to large-scale production, greatly reducing production costs, and improving the safety of organic peroxide production and downstream product production.

In-situ production refers to that the manufacturer places the equipment near the end consumer (or downstream user) or in the same place for production, which greatly reduces the many intermediate links between the manufacturer and the end consumer (or downstream user), such as warehousing, logistics, etc., and saves a lot of costs. However, in-situ production still cannot avoid the storage and transportation of a small number of products, for example, from one workshop of the factory to another, from the production equipment of synthetic products to the downstream production equipment. As a kind of in-situ production, online manufacturing refers to the production mode that products are produced and used at the same time, seamlessly linked with the downstream process and synchronously linked, so as to realize the flexible manufacturing mode of produce-to-use and ready-to-use. To realize online production, plug-and-produce system is needed. The so-called "produce-to-use" means that the output is ready to use, and the production and use of products are carried out at the same time; "ready-to-use" means that the output is ready at any time without waiting, and zero inventory is produced on demand; "plug-and-produce" device means that the product is obtained immediately after the production device is started, and can be produced on demand, and can be stopped after the demand is met. The production time of online production can be shortened to more than 10 minutes or even within a few minutes, which can be seamlessly connected with the production equipment and production process of downstream users, fundamentally avoiding the storage and transportation of products, saving costs, improving the safety of production, and improving production efficiency. The production time refers to the time required from the raw materials entering the reactor to the products conforming to the market, including reaction time and workup time, which is also called residence time in the continuous flow process. As a highly flexible mode of production, online production can not only save a lot of storage, logistics and other costs, but also effectively meet the needs of fast, personalized and customized products, as well as the development direction of the fourth industrial revolution led by industrialization 4.0 and intelligent manufacturing.

In this disclosure, the organic peroxide integrated continuous flow process and reactor can be directly and seamlessly connected to the process and reactor of the downstream end user, realizing produce-to-use and even realizing that there is no accumulation and accumulation process of peroxycarboxylate, peroxycarbonate or peroxyketal in the whole process macroscopically. The integrated continuous flow process can be directly connected with polymerizers in the field of polymer materials, vulcanizers in the film industry, etc., forming a continuous production and use of organic peroxides, subverting the existing production-storage-transport-storage-use production mode, and realizing a new production mode of produce-to-use. The organic peroxides are produced online, produced to-use, produced on demand, zero inventory and no logistics. For example, tert-butyl peroxy 2-ethylhexyl carbonate, as a crosslinking agent, is the most critical core raw material of EVA film in the solar module. The integrated continuous flow reactor of the disclosure can be seamlessly connected with the EVA film vulcanizer. The tert-butyl peroxy 2-ethylhexyl carbonate met the market standard flows out of the integrated continuous flow out reactor and is directly connected with the batching kettle of the vulcanizer, and then the EVA film is obtained by vacuum lamination in the vulcanizer, and finally is cut and packaged. It truly realizes produce-to-use, without any accumulation and storage of 2-ethylhexylcarbonate tert-butyl peroxide. On the one hand, the safety of the whole process is greatly improved. On the other hand, the production cost is further reduced, and the production efficiency is greatly improved.

Organic peroxides are very active compounds, which are easy to decompose into free radicals and oxygen with high reactivity. In this process, a lot of heat will be released and even explode. Therefore, organic peroxides are extremely sensitive to temperature and must be stored and transported at low temperature. There is a large volume of oxidation reaction products (alkyl peroxides) and products (peroxycarboxylates, peroxycarbamates or peroxyketals) during purification, storage and transportation in the existing process, both of which are flammable and explosive organic peroxides. Therefore, ⅓ of the existing production cost of organic peroxides is used for cold-chain storage and transportation of intermediate products and products. Online production is to produce products on demand when they need to be used, that is to say, produce-to-use and ready-to-use production, realizing zero inventory and no transportation of products, which will greatly reduce the cost of inventory and logistics in the production and use of organic peroxides, and also reduce the safety risk to the lowest level. However, the continuous flow process of producing peroxycarboxylate, peroxycarbamate or peroxyketal directly from alcohol or alkane and the plug-and-produce system matching with it cannot be realized in the existing process, so the real online production of the above organic peroxides cannot be achieved, and the huge safety risk and cost in the production and use of the organic peroxides cannot be fundamentally solved and reduced.

Terminology Note:

The term "aryl" as used in this paper refers to a completely conjugated π electron system with 5 to 12 carbon atoms as a whole carbon monocyclic or fused polycyclic group. The non-limiting examples of aromatic ring are benzene ring, naphthalene ring and anthracene ring. Aromatic rings can be unsubstituted or substituted. The substituents of aromatic ring are selected from halogen, nitro, amino, cyano, hydroxy, $C_1$-$C_6$ alkyl, $C_1$-$C_6$ alkoxy, halogenated $C_1$-$C_6$ alkyl, halogenated $C_1$-$C_6$ alkoxy, $C_3$-$C_6$ cycloalkyl, halogenated $C_3$-$C_6$ cycloalkyl.

The term "heterocyclic aryl" as used herein refers to an unsaturated carbon ring of 5 to 12 ring atoms, one or more of which are replaced by heteroatoms such as N, O, S, etc. Heteroaromatic rings can be either single or double rings, that is, they are fused by two rings. Specific heterocyclic aryls can be: pyridyl, pyrimidinyl, pyrazinyl, isoxazolyl, isothiazolyl, pyrazolyl, thiazolyl, oxazolyl and imidazolyl. Heterocyclic aryls may be unsubstituted or substituted. Heterocycloaryl substituents are selected from halogen, nitro, amino, cyano, hydroxy, $C_1$-$C_6$ alkyl, $C_1$-$C_6$ alkoxy, halogenated $C_1$-$C_6$ alkyl, halogenated $C_1$-$C_6$ alkoxy, $C_3$-$C_6$ cycloalkyl, halogenated $C_3$-$C_6$ cycloalkyl.

The term "heterocycloalkyl" as used herein refers to a single ring or fused ring group, in which there are 5 to 12 ring atoms, one or two of which are heteroatoms selected from n, O or $S(O)_m$ (where m is an integer from 0 to 2), and the remaining ring atom is C. These rings may contain one or more double bonds, but they do not have a completely conjugated π electron system. The unsubstituted heterocyclic alkyl group can be pyrrolidine group, piperidinyl group, piperazinyl group, morpholinyl group, thiomorpholinyl group, high piperazinyl group, etc. Heterocycles can be unsubstituted or substituted. Heterocyclic substituents are selected from halogen, nitro, amino, cyano, hydroxy, $C_1$-$C_6$ alkyl, $C_1$-$C_6$ alkoxy, halogenated $C_1$-$C_6$ alkyl, halogenated $C_1$-$C_6$ alkoxy, $C_3$-$C_6$ cycloalkyl, halogenated $C_3$-$C_6$ cycloalkyl.

The term "naphthenic group" as used herein refers to a saturated monocyclic carbon ring with 3 to 12 carbon atoms, unless a different number of atoms is specified. Cycloalkanes include cyclopropyl, cyclobutyl, cyclopentyl, cyclohexyl, cycloheptyl and cyclooctyl. Cycloalkanes may be unsubstituted or substituted. Cycloalkanes may also optionally be substituted on any available carbon by one or more substituents selected from alkoxy, halogen, haloalkanes such as perfluoroalkyl.

The term "alkyl" as used in this patent includes linear alkyl and branched alkyl. If a reference is made to a single alkyl group such as "propyl", it refers only to a linear alkyl group; if a reference is made to a single branched alkyl group such as "isopropyl", it refers only to a branched alkyl group. For example, "$C_1$-$C_6$ alkyl" includes $C_1$-$C_4$ alkyl, $C_1$-$C_3$ alkyl, methyl, ethyl, n-propyl, isopropyl and tert-butyl.

The term "alkoxy" as used in this patent refers to the group containing —O-alkyl group, wherein the alkyl group is as defined above. Examples of "alkoxy" used in the present patent include but are not limited to methoxy, ethoxy, n-propoxy, isopropoxy, n-butoxy and t-butoxy. "Alkoxy" also includes substituted alkoxy groups. Alkoxy groups can be optionally replaced by one or more halogen atoms.

Continuous process refers to the production process in which each step of the production system is connected to each other to ensure continuous operation on the whole, but during each step operation, "stand" is allowed. Continuous flow process, as a continuous process, is a fast and efficient continuous process, which has the characteristics of short time, high efficiency and easy operation. During the whole process, the materials (that is the reaction mixture containing raw materials, intermediates, products, solvents, etc.) continuously flow, without interruption, without standing, that is, the products are continuously produced. It is a kind of "flow-line" chemical production process. When the process operation reaches the steady state, the state parameters such as the composition and temperature of materials at any position in the reactor do not change with time and are a steady-state process, so the production process and product quality are both stable. In a process containing multi reaction steps, if some of the steps are continuous or steps in the batch process are simply connected to each other, the process can be called a semi-continuous process. Only when all steps are continuous and the material flows continuously in the whole process, that is, continuously adding raw materials and continuously obtaining products, can it be called continuous flow process (or whole-process continuous process). The prior art processes for the production of organic peroxides such as peroxycarboxylate, peroxycarbamate, peroxyketal, etc., the oxidation reaction and condensation reaction are carried out respectively. In terms of the whole process, the oxidation and condensation are two separate steps, so they are batch processes.

To solve the problems existing in the existing process, the present disclosure provides an online continuous flow process for the preparation of organic peroxides direct from alcohols or alkanes. The production process takes the very safe material alcohol or alkane as the starting reaction raw material, and produces the organic peroxide successively through two processes of oxidation condensation and workup. The production process is carried out in the plug-and-produce integrated continuous flow reactor, and the reactor substrate, oxidant and condensation agent are continuously added to the feed port of the integrated continuous flow reactor; the organic peroxides of the target product are obtained continuously from the discharge port of the integrated continuous flow reactor. The production process has no amplification effect. The organic peroxides are selected from the carboxylate peroxide, carbamate peroxide and ketal peroxide. The reaction substrate is alcohol or alkane. The condensation agent is alkali liquor and acyl compound in the production of carboxylate peroxide and carbamate peroxide. The condensation agent is acid liquid and condensation raw material in the production of peroxidized ketal; and the condensation raw material is alcohol or ketone.

Through the advantages of integrated reaction process and plug-and-produce integrated continuous flow reactor, the disclosure thoroughly improves the process of organic peroxide production in the prior art, realizes the online continuous flow production of organic peroxide, effectively integrates the oxidation condensation process and workup process into one process. It not only realizes the direct generation of organic peroxides with high degree of danger from safe starting substance (alcohol or alkane), no process of accumulation, purification and standing of dangerous alkyl peroxides (intermediate products) in macroscopical view, and avoids the steps of purification, storage and transportation of alkyl peroxides, achieves the produce-to-use organic peroxides, and also overcomes the problem of amplification effect, realizes the production mode of online manufacturing, production and use of products carried out at the same time, so as to realize the flexible manufacturing mode of produce-to-use and ready-to-use. That is to say, we can produce at any time without standing, zero stock on demand, produce on demand, and then stop when the demand has been met. It not only ensures the high-quality and efficient production of organic peroxides, but also seamlessly connects with the downstream process and synchronously linkage, thus avoiding the storage and transportation steps of the target product organic peroxides, fundamentally solving the cost and safety problems of cold-chain storage and transportation of alkyl peroxides and final products (peroxycarboxylates, peroxycarbamates, peroxyketals).

The general formula of the production process of the disclosure is as follows:

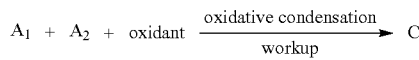

wherein, $A_1$ is alcohol or alkane; $A_2$ is selected from acyl chloride, chloroformate, alcohol and ketone; oxidant is selected from hydrogen peroxide and oxygen; C is selected from carboxylate peroxide, carbamate peroxide and ketal peroxide.

In some embodiments, the general formula of $A_1$ as alcohol is $R(OH)_n$, where n=1, 2, 3 . . . ; the general formula of $A_1$ as alkane is $R(H)_n$, where n=1, 2, 3 . . . ; the general formula of $A_2$ aa acyl chloride is $R^1cocl$; the general formula of $A_2$ as chloroformate is $R^2OCOCl$; the general formula of $A_2$ as alcohol is $R^3(OH)_m$, where m=1, 2, 3 . . . ; the general formula of $A_2$ as ketone is $R^4R^{4'}(CO)$ or $R^4(CO)$ (cyclohexanone); n, m is a positive integer.

The general formula of C as peroxycarboxylate is $R(OOOCR^1)n$, where n=1, 2, 3 . . . ; the general formula of C as peroxycarbonate is $R(OOOCOR^2)n$, where n=1, 2, 3 . . . ; the general formula of C as peroxy ketal is $R^4(OOR)_2$, where n=1; the general formula of C as peroxy ketal is $R^3(OOR)_m$, where n=1, m=1, 2, 3 . . . ; the general formula of C as peroxy ketal is $R(OOR^3)_n$, where m=1, n=1, 2, 3 . . . ; n and m are positive integers.

R is selected from saturated or unsaturated $C_1$-$C_{12}$ alkyl, unsubstituted or substituted aryl, unsubstituted or substituted heterocycloaryl, unsubstituted or substituted saturated heterocycloalkyl, unsubstituted or partially substituted heterocycloalkyl, unsubstituted or substituted cycloalkyl;

$R^1$ is selected from saturated or unsaturated $C_1$-$C_{20}$ alkyl, unsubstituted or substituted aryl, unsubstituted or substituted heterocyclic aryl;

$R^2$ is selected from saturated or unsaturated $C_1$-$C_{20}$ alkyl group, unsubstituted or substituted aryl group, unsubstituted or substituted heterocycloaryl group, unsubstituted or substituted saturated heterocycloalkyl group, unsubstituted or substituted partially substituted heterocycloalkyl group, unsubstituted or substituted cycloalkyl group;

$R^3$ is selected from saturated or unsaturated $C_1$-$C_{12}$ alkyl group, unsubstituted or substituted aryl group, unsubstituted or substituted heterocycloaryl group, unsubstituted or substituted saturated heterocycloalkyl group, unsubstituted or substituted partially substituted heterocycloalkyl group, unsubstituted or substituted cycloalkyl group;

$R^4$ or $R^{4'}$ is selected from saturated or unsaturated $C_1$-$C_{12}$ alkyl, unsubstituted or substituted aryl, unsubstituted or substituted heterocycloaryl, unsubstituted or substituted saturated heterocycloalkyl, unsubstituted or substituted partially saturated heterocycloalkyl, unsubstituted or substituted cycloalkyl;

Preferably,

R selected from saturated or unsaturated $C_3$-$C_8$ alkyl group, unsubstituted or substituted aryl group, unsubstituted or substituted heterocyclic aryl group, unsubstituted or substituted saturated heterocyclic group, unsubstituted or partially substituted heterocyclic group, unsubstituted or substituted cycloalkane group;

$R^1$ is selected from saturated or unsaturated $C_1$-$C_{18}$ alkyl, unsubstituted or substituted aryl, unsubstituted or substituted heterocyclic aryl;

$R^2$ is selected from saturated or unsaturated $C_1$-$C_{18}$ alkyl, unsubstituted or substituted aryl, unsubstituted or substituted heterocyclic aryl, unsubstituted or substituted saturated heterocyclic, unsubstituted or substituted partially substituted heterocyclic, unsubstituted or substituted cycloalkane;

$R^3$ is selected from saturated or unsaturated $C_3$-$C_8$ alkyl, unsubstituted or substituted aryl, unsubstituted or substituted heterocyclic aryl, unsubstituted or substituted saturated heterocyclic, unsubstituted or substituted partially saturated heterocyclic, unsubstituted or substituted cycloalkane;

$R^4$ or $R^{4'}$ is selected from saturated or unsaturated $C_3$-$C_8$ alkyl, unsubstituted or substituted aryl, unsubstituted or saturated heterocyclic, unsubstituted or substituted partially saturated heterocyclic, unsubstituted or substituted cycloalkane;

More preferably,

R is selected from tert-butyl, tert-amyl, isopropyl phenyl, 1,4-diisopropyl, 2,4,4-trimethyl-2-amyl, 2,5-dimethylhexyl, 1,3-diisopropyl;

$R^1$ is selected from methyl, ethyl, propyl, isopropyl, butyl, sec-butyl, tert-butyl, isoamyl, n-amyl, isoheptyl, octyl, isooctyl, 2,2-dimethylheptyl, nonyl, undecyl, phenyl, 2-methylphenyl, 4-methylphenyl, 4-chlorophenyl, 2,4-di chlorophenyl, naphthyl;

$R^2$ is selected from methyl, ethyl, propyl, isopropyl, butyl, sec-butyl, 2-ethylhexyl, isotridecyl, heptadecyl, cyclohexyl, 4-tert-butyl cyclohexyl, benzyl, phenoxyethyl;

$R^3$ is selected from tert-butyl, tert-amyl, 2,5-dimethylhexyl, 1,4-diisopropylphenyl, 1,3-diisopropylphenyl;

$R^4$ or $R^{4'}$ is selected from methyl and ethyl; $R^4$ is selected from —$(CH_2)_5$—, —$CH_2$—$C(CH_3)_2$—$CH_2$—$C(CH_3)$—$CH_2$—;

More preferably, $R(OH)_n$ is selected from tert-butanol, tert-amyl alcohol, 2,4,4-trimethyl-2-pentanol, 2,5-dimethyl-2,5-dihydroxyhexane, dihydroxy-1,4-diisopropylbenzene and dihydroxy-1,3-diisopropylbenzene;

$R(H)_n$ was selected from isopropylbenzene, 1,4-diisopropylbenzene and 1,3-diisopropylbenzene;

$R^1COCl$ is selected from acetyl chloride, propionyl chloride, butyryl chloride, isobutyryl chloride, valeryl chloride, 2-methylbutyryl chloride, neopentyl chloride, 2-methylvaleryl chloride, 2-ethylbutyryl chloride, 2-ethylhexyl chloride, nonyl chloride, 2,4,4-trimethylvaleryl chloride, 3,5,5-trimethylhexyl chloride, neopentyl chloride, decanoyl chloride, lauroyl chloride, benzoyl chloride, 2-methylbenzoyl chloride, 4-methylbenzoyl chloride, 4-chlorobenzoyl chloride, 2,4-dichlorobenzoyl chloride, naphthalene formyl chloride;

$R^2OCOCl$ is selected from methyl chloroformate, ethyl chloroformate, n-propyl chloroformate, isopropyl chloroformate, n-butyl chloroformate, sec-butyl chloroformate, 2-ethylhexyl chloroformate, isotridecyl chloroformate, stearyl chloroformate, cyclohexyl chloroformate, 4-tert-butyl cyclohexyl chloroformate, benzyl Chloroformate and 2-phenoxyethyl chloroformate;

$R^3(OH)_n$ is selected from tert-butanol, tert-amyl alcohol, 2,4,4-trimethyl-2-pentanol, 2,5-dimethyl-2,5-dihydroxyhexane, dihydroxy-1,4-diisopropylbenzene and dihydroxy-1,3-diisopropylbenzene;

$R^4R^{4'}(CO)$ is selected from methyl ethyl ketone; $R^4(CO)$ is selected from cyclohexanone, 3,3,5-trimethylcyclohexanone.

In some embodiments, the organic peroxide is selected from:

t-butyl peroxybenzoate CAS No.: 614-45-9, t-amyl peroxybenzoate CAS No.: 4511-39-1, t-butyl peroxyacetate CAS No.: 107-71-1, t-butyl terephentate peroxide CAS No.: 927-07-1, t-amyl terephentate peroxide CAS No.: 29240-17-3, t-butyl peroxyneodecanoate CAS No.: 26748-41-4, t-amyl peroxyneodecanoate CAS No.: 68299-16-1, t-butyl peroxide 2-ethylcaproate CAS No.: 3006-82-4, t-amyl peroxide 2-ethylcaproate CAS No.: 686-31-7, t-butyl isobutyrate peroxide CAS No.: 109-13-7, t-butyl neoheptanoate peroxide CAS No.: 26748-38-9, t-butyl 3,5,5-trimethylhexanoate peroxide CAS No.: 13122-18-4, t-butyl 2-ethylhexanoate peroxide CAS No.: 34443-12-4, t-butyl 2-ethylhexanoate peroxide t-amyl carbonate CAS No.: 70833-40-8, 1,1-di-tert-butyl peroxide-3,3,5-trimethylcyclohexane CAS No.: 6731-36-8, 1,1-di(tert-butyl peroxide) cyclohexane CAS No.: 3006-86-8, 2,2-di(tert-butyl peroxide) butane CAS No.: 2167-23-9, isopropylphenyl peroxyneodecanoate CAS No.: 26748-47-0, 1,1,3,3-tetramethylbutyl peroxyneodecanoate CAS No.: 51240-95-0 1,1,3,3-tetramethylbutyl peroxypivalate CAS No.: 22288-41-1, 1,1,3,3-tetramethylbutyl peroxy-2-ethylhexanoate CAS No.: 22288-43-3, 1,1-bis (tert-amty peroxy) cyclohexane CAS No.: 15667-10-4, t-amyl acetate peroxide CAS No.: 690-83-5, t-butyl isopropyl carbonate peroxide CAS No.: 2372-21-6, t-butyl peroxide isopropylbenzene CAS No.: 3457-61-2.

The production process of the disclosure has no dangerous process of accumulation, purification and stand waiting of alkyl peroxides (intermediate products), realizes the continuous production of organic peroxides (peroxycarboxylates, peroxycarbamates, peroxyketals) with alcohol or alkanes as the starting reaction substrate, and innovatively realizes the online production of organic peroxides, i.e. produce to use. It breaks through the limitations of the existing technology.

The general formula of the alkyl peroxide is $R(OOH)_n$, wherein R is selected from saturated or unsaturated $C_1$-$C_{12}$ alkyl, unsubstituted or substituted aryl, unsubstituted or substituted heterocyclic aryl, unsubstituted or substituted saturated heterocyclic, unsubstituted or partially saturated heterocyclic, unsubstituted or substituted naphthenic, n≥1, and n is a positive integer.

In some embodiments, R is selected from saturated or unsaturated $C_3$-$C_8$ alkyl, unsubstituted or substituted aryl, unsubstituted or substituted heterocyclic aryl, unsubstituted or substituted saturated heterocyclic, unsubstituted or partially saturated heterocyclic, unsubstituted or substituted cycloalkane.

In some embodiments, R is selected from tert-butyl, tert-amyl, isopropyl phenyl, 1,4-diisopropyl, 2,4,4-trimethyl-2-amyl, 2,5-dimethylhexyl.

In some embodiments, alkyl peroxides are selected from:

t-butyl hydroperoxides CAS No.: 75-91-2, tert-amyl hydroperoxides CAS No.: 3425-61-4, CAS No.: 4212-43-5, 1, 1, 3, 3-tetramethyl-butyl hydroperoxides CAS No.: 5809-08-5, cumene hydroperoxides CAS No.: 80-15-9, 2, 5-dimethyl-2, 5-bis (hydroperoxides) hexane CAS No.: 3025-88-5, dihydroxy-1, 4-diisopropylbenzene CAS No.: 3159-98-6.

The target product organic peroxide produced by the process of the disclosure is a product conforming to the standards of commercial industrial products. In some embodiments, the content of chloride ion in the target product organic peroxide is ≤0.05 wt. %, and the content of other organic peroxide impurities is ≤0.1 wt. %. The other organic peroxide impurities are selected from any one or any many of $H_2O_2$, alkyl peroxide and dialkyl peroxide.

In some embodiments, the production time of the process of the disclosure is ≤15 min, the preferred production time is ≤10 min; more preferably, the production time is 3-13 min; more preferably, the production time is 4-11 min; more preferably, the production time is 5-10 min. The production time refers to the time required from the entry of reaction raw materials (reaction substrate, oxidant and condensation agent) into the integrated continuous flow reactor to the output of the target product meeting the market standard, including the time of oxidation condensation process and workup process.

In some embodiments, the yield of the organic peroxide is ≥64%; preferably, the yield of the organic peroxide is ≥75%; more preferably, the yield of the organic peroxide is ≥81%.

In some embodiments, the content of the organic peroxide is ≥77%; preferably, the content of the organic peroxide is ≥85%; and the content of the organic peroxide is ≥97%.

In some embodiments, the temperature of the oxidation condensation process is 0 to 200° C., preferably 0 to 180° C., more preferably 0 to 160° C., more preferably 0 to 140° C., more preferably 5 to 130° C.

In some embodiments, the workup temperature is 0 to 60° C., preferably 0 to 50° C., more preferably 0 to 40° C., more preferably 0 to 30° C., more preferably 5 to 30° C.

In some embodiments, the alkali is selected from water-soluble metal hydroxide, water-soluble quaternary ammonium hydroxide, water-soluble tertiary amine, water-soluble metal carbonate or water-soluble metal phosphate, preferably alkali metal hydroxide, alkali earth metal hydroxide or water-soluble metal carbonate, more preferably sodium hydroxide, potassium hydroxide, sodium carbonate, potassium carbonate or lithium hydroxide.

In some embodiments, the mass concentration of alkali liquor is 5% to 45%, preferably 15% to 35%, more preferably 20% to 30%.

In some embodiments, the acid is selected from all known organic and inorganic acids, preferably sulfuric acid, phosphoric acid or trifluoroacetic acid.

In some embodiments, the mass concentration of the acid solution is 50% to 90%, preferably 60% to 80%, more preferably 70% to 80%.

In some embodiments, the oxidant is selected from hydrogen peroxide and oxygen.

In some embodiments, the reaction substrate is selected from tert-butanol, tert-amyl alcohol, isopropyl benzene, 1,4-diisopropylbenzene, p-mentane, pinane, tetrahydronaphthalene, 2,4,4-trimethyl-2-pentanol, 1,3-diisopropylbenzene, dihydroxy-1,4-diisopropylbenzene and dihydroxy-1,3-diisopropylbenzene.

In some embodiments, the acyl compounds in the condensation agent are selected from acetyl chloride, propionyl chloride, butyryl chloride, isobutyryl chloride, valeryl chloride, 2-methylbutyryl chloride, neopentyl chloride, 2-methylglutaryl chloride, 2-ethylbutyryl chloride, 2-ethylhexyl chloride, nonyl chloride, 2,4,4-trimethylglutaryl chloride, 3,5,5-trimethylhexyl chloride, neodecanoyl chloride, decanoyl chloride, lauroyl chloride, benzoyl chloride, 2-methylbenzoyl chloride, 4-methylbenzoyl chloride, 4-chlorobenzoyl chloride, 2,4-dichlorobenzoyl chloride, naphthoyl chloride, methyl chloroformate, ethyl chloroformate, n-propyl chloroformate, isopropyl chloroformate, n-butyl chloroformate, sec-butyl chloroformate, 2-ethylhexyl chloroformate, isotridecyl chloroformate, stearyl chloroformate, cyclohexyl chloroformate, 4-tert-butyl cyclohexyl chloroformate, benzyl chloroformate and 2-phenoxyethyl chloroformate; the alcohol in the condensation agent is selected from tert-butanol and tert-amyl alcohol; the ketone in the condensation agent is selected from cyclohexanone, 3,3,5-trimethylcyclohexanone and methyl ethyl ketone.

In some embodiments, the molar ratio of acid to reaction substrate is 0.3:1 to 1.5:1, preferably 0.4:1 to 1.2:1, more preferably 0.5:1 to 1:1.

In some embodiments, the molar ratio of oxidant and reaction substrate is 0.8:1 to 2.2:1, preferably 0.9:1 to 2.1:1, more preferably 1:1 to 2:1, more preferably 1.3:1 to 1.8:1.

In some embodiments, the molar ratio of alkali to reaction substrate is 0.7:1 to 2:1, preferably 0.9:1 to 1.8:1, more preferably 1:1 to 1.6:1, more preferably 1:1 to 1.4:1.

In some embodiments, the molar ratio of acyl compound and reaction substrate is 0.5:1 to 1.2:1, preferably 0.6:1 to 1.1:1, more preferably 0.7:1 to 1:1.

In some embodiments, the molar ratio of condensation raw material and reaction substrate is 0.5:1 to 1.2:1, preferably 0.6:1 to 1.1:1, more preferably 0.7:1 to 1:1.

In some embodiments, the reaction bottom flow rate is 0.2 to 10 L/h, preferably 0.5 to 8 L/h, more preferably 1 to 6 L/h.

In some embodiments, the acid flow rate is 0.2 to 5 L/h, preferably 0.4 to 4 L/h, more preferably 0.5 to 3 L/h.

In some embodiments, the flow rate of the alkali liquor is 0.2 to 12 L/h, preferably 0.3 to 9 L/h, more preferably 0.5 to 8 L/h.

In some embodiments, the flow rate of the acyl compound or condensation raw material is 0.2 to 8 L/h, preferably 0.3 to 6 L/h, more preferably 0.5 to 4 L/h.

In some embodiments, the target product of the online continuous flow production process is tert-butyl peroxyneodecanoate, the reaction substrate is tert-butanol, the acyl compound is neodecanoyl chloride, and the oxidant is hydrogen peroxide, wherein, preferably:

The mass concentration of the hydrogen peroxide is 30% to 50%.

The production time of the production process is ≤10 min, preferably, the production time is 3 to 9 min; more preferably, the production time is 4 to 8 min; more preferably, the production time is 5 to 7 min.

The yield of tert-butyl peroxyneodecanoate is ≥68%; preferably, the yield of tert-butyl peroxyneodecanoate is ≥81%.

The content of tert-butyl peroxyneodecanoate ≥87%; preferably, the content of tert-butyl peroxyneodecanoate ≥91%.

The content of chloride ion in tert-butyl peroxyneodecanoate of the target product is 0.03 to 0.05 wt. %, the content of other organic peroxide impurities is 0.05 to 0.08 wt. %, and the other organic peroxide impurities are $H_2O_2$ and di tert-butyl peroxides.

The temperature of the oxidation condensation process is 0 to 160° C., preferably 20 to 130° C., more preferably 40 to 120° C., more preferably 60 to 100° C., more preferably 70 to 90° C.

The workup temperature is 0 to 50° C., preferably 0 to 40° C., more preferably 5 to 30° C., more preferably 5 to 20° C.

The flow rate of tert-butanol is 1 to 8 L/h, preferably 1.5 to 6 L/h, more preferably 2 to 4 L/h.

The acid flow rate is 0.4 to 5 L/h, preferably 0.5 to 4 L/h, more preferably 1 to 3 L/h, more preferably 1.5 to 2.5 L/h.

The flow rate of the alkali liquor is 0.4 to 9 L/h, preferably 0.8 to 7 L/h, more preferably 1 to 6 L/h, more preferably 1.2 to 5 L/h, more preferably 1.5 to 3 L/h.

The flow rate of the new decanoyl chloride is 0.4 to 7 L/h, preferably 0.8 to 6 L/h, more preferably 1 to 5 L/h, more preferably 1.5 to 4 L/h, more preferably 2 to 3 L/h.

The molar ratio of the acid and tert-butanol is 0.3:1 to 1.3:1, preferably 0.4:1 to 1.2:1, more preferably 0.5:1 to 1:1, more preferably 0.5:1 to 0.8:1.

The molar ratio of the hydrogen peroxide and tert-butanol is 0.8:1 to 1.5:1, preferably 0.9:1 to 1.4:1, more preferably 1:1 to 1.3:1, more preferably 1.05:1 to 1.2:1.

The molar ratio of the alkali and tert-butanol is 0.9:1 to 1.6:1, preferably 1:1 to 1.4:1, more preferably 1.2:1 to 1.3:1.

The molar ratio of the new decanoyl chloride and tert-butanol is 0.5:1 to 1.1:1, preferably 0.6:1 to 1:1, more preferably 0.7:1 to 0.9:1.

The alkali is selected from water-soluble metal hydroxide, water-soluble quaternary ammonium hydroxide, water-soluble tertiary amine, water-soluble metal carbonate or water-soluble metal phosphate, preferably alkaline metal hydroxide, alkaline earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

In some embodiments, when the target product of the online continuous flow production process is peroxidized neodecanoic acid-1,1,3,3-tetramethyl butyl ester, the reaction substrate is 2,4,4-trimethyl-2-pentanol; the acyl compound is neodecanoyl chloride; and the oxidant is hydrogen peroxide, wherein, preferably:

The mass concentration of the hydrogen peroxide is 30% to 50%.

The production time of the production process is ≤10 min, preferably, the production time is 3 to 9 min; more preferably, the production time is 4 to 8 min; more preferably, the production time is 5 to 7 min.

The yield of neodecanoic acid-1,1,3,3-tetramethyl butyl peroxide is ≥65%; preferably, the yield of neodecanoic acid-1,1,3,3-tetramethyl butyl peroxide is ≥70%.

The content of neodecanoic acid-1,1,3,3-tetramethyl butyl peroxide is ≥80%; preferably, the content of neodecanoic acid-1,1,3,3-tetramethyl butyl peroxide is ≥90%.

The content of chloride ion in neodecanoic acid-1,1,3,3-tetramethyl butyl peroxide of the target product is 0.03 to 0.05 wt %, the content of other organic peroxide impurities is 0.05 to 0.1 wt %, and the other organic peroxide impurities are $H_2O_2$.

The temperature of the oxidation condensation process is 0 to 160° C., preferably 20 to 130° C., more preferably 40 to 120° C., more preferably 60 to 100° C., more preferably 70 to 90° C.

The workup temperature is 0 to 50° C., preferably 0 to 40° C., more preferably 5 to 30° C., more preferably 5 to 20° C.

The flow rate of the 2,4,4-trimethyl-2-pentanol is 1 to 8 L/h, preferably 1.5 to 6 L/h, more preferably 2 to 4 L/h.

The acid flow rate is 0.4 to 5 L/h, preferably 0.5 to 4 L/h, more preferably 1 to 3 L/h, more preferably 1.5 to 2.5 L/h.

The flow rate of the alkali liquor is 0.4 to 11 L/h, preferably 0.8 to 7 L/h, more preferably 1 to 6 L/h, more preferably 1.2 to 5 L/h, more preferably 1.5 to 3 L/h.

The flow rate of the new decanoyl chloride is 0.4 to 7 L/h, preferably 0.8 to 6l/h, more preferably 1 to 5 L/h, more preferably 1.5 to 4 L/h, more preferably 2 to 3 L/h.

The molar ratio of the acid to 2,4,4-trimethyl-2-pentanol is 0.3:1 to 1.3:1, preferably 0.4:1 to 1.2:1, more preferably 0.5:1 to 1:1, more preferably 0.5:1 to 0.8:1.

The molar ratio of the hydrogen peroxide and 2,4,4-trimethyl-2-pentanol is 0.8:1 to 1.5:1, preferably 0.9:1 to 1.4:1, more preferably 1:1 to 1.3:1, more preferably 1.05:1 to 1.2:1.

The molar ratio of the base and 2,4,4-trimethyl-2-pentanol is 0.9:1 to 1.6:1, preferably 1:1 to 1.4:1, more preferably 1.2:1 to 1.3:1.

The molar ratio of the neodecanoyl chloride and 2,4,4-trimethyl-2-pentanol is 0.7:1 to 1.1:1, preferably 0.8:1 to 1:1, more preferably 0.8:1 to 0.95:1.

The alkali is selected from water-soluble metal hydroxide, water-soluble quaternary ammonium hydroxide, water-soluble tertiary amine, water-soluble metal carbonate or water-soluble metal phosphate, preferably alkali metal hydroxide, alkali earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

In some embodiments, the target product of the online continuous flow production process is tert-butyl peroxide 2-ethylhexyl carbonate, the reaction substrate is tert-butanol, the acyl compound is 2-ethylhexyl chloroformate, and the oxidant is hydrogen peroxide, wherein, preferably:

The mass concentration of the hydrogen peroxide is 30% to 50%.

The production time of the production process is ≤10 min, preferably, the production time is 3 to 9 min; more preferably, the production time is 4 to 8 min; more preferably, the production time is 5 to 7 min.

The yield of the 2-ethylhexylcarbonate tert-butyl peroxide is ≥70%; preferably, the yield of the 2-ethylhexylcarbonate tert-butyl peroxide is ≥81%.

The content of the 2-ethylhexylcarbonate tert-butyl peroxide is ≥95%; preferably, the content of the 2-ethylhexylcarbonate tert-butyl peroxide is ≥97%.

The content of chloride ion in the target product tert-butyl peroxide is 0.03 to 0.05 wt %, the content of other organic peroxide impurities is 0.05 to 0.08 wt %, and the other organic peroxide impurities are $H_2O_2$ and ditert-butyl peroxide.

The temperature of the oxidation condensation process is 0 to 160° C., preferably 20 to 130° C., more preferably 40 to 120° C., more preferably 60 to 100° C., more preferably 70 to 90° C.

The workup temperature is 0 to 50° C., preferably 0 to 40° C., more preferably 5 to 30° C., more preferably 5 to 20° C.

The flow rate of tert-butanol is 1 to 8 L/h, preferably 1.5 to 6 L/h, more preferably 2 to 4 L/h.

The acid flow rate is 0.4 to 5 L/h, preferably 0.5 to 4 L/h, more preferably 1 to 3 L/h, more preferably 1.5 to 2.5 L/h.

The flow rate of the alkali liquor is 0.4 to 9 L/h, preferably 0.8 to 7 L/h, more preferably 1 to 6 L/h, more preferably 1.2 to 5 L/h, more preferably 1.5 to 3 L/h.

The flow rate of 2-ethylhexyl chloroformate is 0.4 to 7 L/h, preferably 0.8 to 6 L/h, more preferably 1 to 5 L/h, more preferably 1.5 to 4 L/h, more preferably 2 to 3 L/h.

The molar ratio of the acid and tert-butanol is 0.3:1 to 1.3:1, preferably 0.4:1 to 1.2:1, more preferably 0.5:1 to 1:1, more preferably 0.5:1 to 0.8:1.

The molar ratio of the hydrogen peroxide and tert-butanol is 0.8:1 to 1.5:1, preferably 0.9:1 to 1.4:1, more preferably 1:1 to 1.3:1, more preferably 1.05:1 to 1.2:1.

The molar ratio of the alkali and tert-butanol is 0.9:1 to 1.6:1, preferably 1:1 to 1.4:1, more preferably 1.2:1 to 1.3:1.

The molar ratio of 2-ethylhexyl chloroformate and tert-butanol is 0.5:1 to 1.1:1, preferably 0.6:1 to 1:1, more preferably 0.7:1 to 0.9:1.

The alkali is selected from water-soluble metal hydroxide, water-soluble quaternary ammonium hydroxide, water-soluble tertiary amine, water-soluble metal carbonate or water-soluble metal phosphate, preferably alkali metal hydroxide, alkali earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

In some embodiments, the target product of the online continuous flow production process is isopropyl peroxyneodecanoate, the reaction substrate is isopropyl benzene, the acyl compound is neodecanoyl chloride, and the oxidant is oxygen, wherein, preferably:

The production time of the production process is ≤10 min, preferably, the production time is 3 to 9 min; more preferably, the production time is 4 to 8 min; more preferably, the production time is 5 to 7 min.

The yield of the isopropyl neodecanoate peroxide is ≥79%; preferably, the yield of the isopropyl neodecanoate peroxide is ≥81%.

The content of the isopropyl peroxyneodecanoate is ≥89%; preferably, the content of the isopropyl peroxyneodecanoate is ≥94%.

The content of chloride ion in the target product isopropyl neodecanoate is 0.03 to 0.05 wt %, the content of other organic peroxide impurities is 0.05 to 0.1 wt %, and the other peroxide impurities are diisopropylbenzene hydroperoxides.

The temperature of the oxidation condensation process is 0 to 180° C., preferably 0 to 150° C., preferably 20 to 130° C., more preferably 40 to 120° C., more preferably 60 to 100° C., more preferably 70 to 90° C.

The workup temperature is 0 to 60° C., preferably 0 to 50° C., more preferably 0 to 40° C., more preferably 0 to 30° C., more preferably 5 to 30° C.

The flow rate of the cumene is 0.2 to 8 L/h, preferably 0.5 to 6 L/h, more preferably 1.5 to 4 L/h, more preferably 2 to 3 L/h.

The flow rate of the alkali liquor is 0.4 to 9 L/h, preferably 0.8 to 7 L/h, more preferably 1 to 6 l/h, more preferably 1.2 to 5 L/h, more preferably 1.5 to 3 L/h.

The flow rate of the new decanoyl chloride is 0.4 to 7 L/h, preferably 0.8 to 6 L/h, more preferably 1 to 5 L/h, more preferably 1.5 to 4 L/h, more preferably 2 to 3 L/h.

The molar ratio of the oxygen and cumene is 0.8:1 to 2.2:1, preferably 1.3:1 to 2.1:1, more preferably 1.5:1 to 2:1.

The molar ratio of the alkali and cumene is 1:1 to 1.8:1, preferably 1.2:1 to 1.6:1, more preferably 1.3:1 to 1.5:1.

The molar ratio of the new Decanoyl chloride and cumene is 0.5:1 to 1.1:1, preferably 0.6:1 to 1:1, more preferably 0.7:1 to 0.9:1.

The alkali is selected from water-soluble metal hydroxide, water-soluble quaternary ammonium hydroxide, water-soluble tertiary amine, water-soluble metal carbonate, water-soluble metal phosphate, preferably alkali metal hydroxide, alkali earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

In some embodiments, the target product of the online continuous flow production process is tert-butyl peroxide isopropyl carbonate, the reaction substrate is tert-butanol, the acyl compound is isopropyl chloroformate, and the oxidant is hydrogen peroxide, wherein, preferably:

The mass concentration of the hydrogen peroxide is 30% to 50%.

The production time of the production process is ≤10 min, preferably, the production time is 3 to 9 min; more preferably, the production time is 4 to 8 min; more preferably, the production time is 5 to 7 min.

The yield of the tert-butyl peroxide isopropyl carbonate is ≥70.5%; preferably, the yield of the tert-butyl peroxide isopropyl carbonate is ≥80%.

The content of tert-butyl peroxide isopropyl carbonate is ≥95%; preferably, the content of tert-butyl peroxide isopropyl carbonate is ≥97%.

The content of chloride ion in the target product is 0.03 to 0.05 wt %, the content of other organic peroxide impurities is 0.05 to 0.08 wt %, and the other organic peroxide impurities are $H_2O_2$ and di tert-butyl peroxide.

The temperature of the oxidation condensation process is 0 to 160° C., preferably 20 to 130° C., more preferably 40 to 120° C., more preferably 60 to 100° C., more preferably 70 to 90° C.

The workup temperature is 0 to 50° C., preferably 0 to 40° C., more preferably 5 to 30° C., more preferably 5 to 20° C.

The molar ratio of the acid and tert-butanol is 0.3:1 to 1.3:1, preferably 0.4:1 to 1.2:1, more preferably 0.5:1 to 1:1, more preferably 0.5:1 to 0.8:1.

The molar ratio of the hydrogen peroxide and tert-butanol is 0.8:1 to 1.5:1, preferably 0.9:1 to 1.4:1, more preferably 1:1 to 1.3:1, more preferably 1.05:1 to 1.2:1.

The molar ratio of the alkali and tert-butanol is 0.9:1 to 1.6:1, preferably 1:1 to 1.4:1, more preferably 1.2:1 to 1.3:1.

The molar ratio of isopropyl chloroformate and tert-butanol is 0.5:1 to 1.1:1, preferably 0.6:1 to 1:1, more preferably 0.7:1 to 0.9:1.

The alkali is selected from water-soluble metal hydroxide, water-soluble quaternary ammonium hydroxide, water-soluble tertiary amine, water-soluble metal carbonate, water-soluble metal phosphate, preferably alkali metal hydroxide, alkali earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

In some embodiments, the target product of the online continuous flow production process is tert-amyl peroxide 2-ethylhexyl carbonate, the reaction substrate is tert-amyl alcohol, the acyl compound is 2-ethylhexyl chloroformate, and the oxidant is hydrogen peroxide, wherein, preferably:

The mass concentration of the hydrogen peroxide is 30% to 50%.

The production time of the production process is ≤10 min, preferably, the production time is 3-9 min; more preferably, the production time is 4 to 8 min; more preferably, the production time is 5 to 7 min.

The content of chloride ion in the target product tert-amyl peroxide is 0.03 to 0.05 wt %, the content of other organic peroxide impurities is 0.05 to 0.08 wt %, and the other organic peroxide impurities are $H_2O_2$ and tert-amyl peroxide.

The temperature of the oxidation condensation process is 0 to 160° C., preferably 20 to 130° C., more preferably 40 to 120° C., more preferably 60 to 100° C., more preferably 70 to 90° C.

The workup temperature is 0 to 50° C., preferably 0 to 40° C., more preferably 5 to 30° C., more preferably 5 to 20° C.

The yield of the 2-ethylhexyl carbonate tert-amyl peroxide is ≥70%; preferably, the yield of the 2-ethylhexyl carbonate tert-amyl peroxide is ≥81%.

The content of the 2-ethylhexylcarbonate tert-amyl peroxide ≥95%; preferably, the content of the 2-ethylhexylcarbonate tert-amyl peroxide ≥97%

The molar ratio of the acid and tert-amyl alcohol is 0.3:1 to 1.3:1, preferably 0.4:1 to 1.2:1, more preferably 0.5:1 to 1:1, more preferably 0.5:1 to 0.8:1.

The molar ratio of the hydrogen peroxide and tert-amyl alcohol is 0.8:1 to 1.5:1, preferably 0.9:1 to 1.4:1, more preferably 1:1 to 1.3:1, more preferably 1.05:1 to 1.2:1.

The molar ratio of the alkali and tert-amyl alcohol is 0.9:1 to 1.6:1, preferably 1:1 to 1.4:1, more preferably 1.2:1 to 1.3:1.

The molar ratio of 2-ethylhexyl chloroformate and tert-amyl alcohol is 0.5:1 to 1.1:1, preferably 0.6:1 to 1:1, more preferably 0.7:1 to 0.9:1.

The alkali is selected from water-soluble metal hydroxide, water-soluble quaternary ammonium hydroxide, water-soluble tertiary amine, water-soluble metal carbonate, water-soluble metal phosphate, preferably alkali metal hydroxide, alkali earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

It should be noted that the mass concentration of reaction substrate, oxidant and condensation agent used in actual production (including laboratory, pilot test and actual production process) will have a deviation of ±3 percentage; the temperature in the temperature zone will have a deviation of ±3° C.; the production time will have a deviation of ±3 s.

Because the solution of the disclosure uses the very safe material as the starting material to produce organic peroxides, there is no alkyl peroxide during the process, so there is no need to purify and store the dangerous oxidation product—alkyl peroxides, and the final product is produced-to-use, without storing risk of a large number of alkyl peroxides and products (peroxycarboxylates, peroxycarbamates and peroxides ketone. has no amplification effect at the same time, which greatly reduces the difficulty of industrial application. When it is expanded to industrialization, it can be enlarged to the required production scale at one time without the tedious and complex multiple step-by-step amplification and the adjustment and optimization of process conditions and parameters, which greatly saves human resources and project development time; in industrial production, it can be flexible The production scale of the product can be changed flexibly without readjusting and optimizing the process conditions and parameters, and the production process is flexible; the production process is stable and reliable without amplification effect, and the fluctuation of the process conditions and parameters will not affect the product quality, and the product quality is easy to control; this also greatly improves the safety of the production process.

The continuous flow process of the disclosure has good stability and reliability, so the product quality is stable and the reproducibility is good; the process has no amplification effect, and solves the problem of amplification effect existing in the industrialization of organic peroxide continuous flow process; at the same time, the plug-and-produce integrated continuous flow reactor has the advantages of short production time, small volume, small floor area, and great saving due to no need of delay pipeline, so that the land for workshop and production efficiency are increased.

To meet the operational conditions of the continuous flow process of the disclosure, the disclosure develops a special integrated reactor. The reactor can be a modular structure, which needs to design the organization and quantity of the modules, the modules contained in each temperature zone, as well as the development of targeted process conditions and parameters, including the division of each temperature zone and the temperature setting. All the above factors have a synergistic effect, so that the continuous flow process can be realized. In addition, the temperature, material concentration, material ratio and material flow rate can be further combined to make them match the reaction process and get better reaction effect.

The production process of the disclosure can rapidly and continuously complete the reaction of preparing organic peroxides under high temperature. The total reaction time can be shortened to 15 minutes or even to several minutes by using the optimization of functional unit division, temperature setting and the synergy of functional units, which greatly improves the efficiency of the process. It can be seen that the production process of the disclosure breaks through the limitation of the prior art. Under the harsh and dangerous conditions that the prior art cannot realize, the production of organic peroxides with high efficiency and quality is successfully realized, the steps of purification, storage and transportation of alkyl peroxides are avoided, and the immediate production and use of organic peroxides are realized, which not only ensures the high quality of organic peroxides efficient production, seamless connection and simultaneous linkage with the downstream process, thus avoiding the storage and transportation steps of the target product organic peroxide. And the production process has no amplification effect, which is very suitable for industrial production, and can realize the produce-to-use of organic peroxides without cold chain transportation and storage, greatly improving the safety of production and use and reducing the cost, which is a major breakthrough in the field.

In some embodiments, in order to match the continuous flow production process of organic peroxides, the plug-and-produce integrated continuous flow reactor adopts a unit structure, including an oxidation condensation unit and a workup unit, wherein the oxidation condensation unit is used to realize the reaction of reaction substrate, oxidant and condensation agent to generate peroxycarboxylate, peroxycarbamate and peroxyketal. The workup unit is used for the purification and cleaning of the organic peroxide, which is selected from the carboxylate peroxide, carbamate peroxide and ketal peroxide.

In some embodiments, the temperature of the oxidation condensation unit is 0 to 200° C., preferably 0 to 180° C., more preferably 0 to 160° C., more preferably 0 to 140° C., more preferably 5 to 130° C.

In some embodiments, the temperature of the workup unit is 0 to 60° C., preferably 0 to 50° C., more preferably 0 to 40° C., more preferably 0 to 30° C., more preferably 5 to 30° C.

In some embodiments, in order to match the continuous flow production process of organic peroxides, the plug-and-produce integrated continuous flow reactor adopts a unit structure, each unit independently comprises more than one reactor module or reactor module group, wherein the reactor module group is composed of multiple reactor modules in series or in parallel, and each unit is in series with each other.

In some embodiments, in order to match the continuous flow production process of organic peroxides, the plug-and-produce integrated continuous flow reactor adopts a cellular structure, each of which comprises at least one temperature zone, each of which independently comprises more than one reactor module or reactor module group, wherein the reactor module group is composed of multiple reactor modules in series or in parallel, the temperature zones are connected in series.

In some embodiments, the buffer vessel is further included between the units. The buffer is a container with a certain volume, which is mainly used to buffer the pressure fluctuation and balance the flow difference of the system, so as to make the system work more smoothly.

In some embodiments, the number of the feed ports of the integrated continuous flow reactor is one or more, and the number of the discharge ports of the integrated continuous flow reactor is one or more.

In some embodiments, the reactor module is any reactor capable of realizing continuous flow process, and the reactor is any one or any multiple of microreactor, tandem loop reactor and tubular reactor. The micro reactor, also known as micro structure reactor or micro channel reactor, is a kind of equipment in which chemical reaction takes place in a limited area with a general lateral dimension of 1 mm or less. The most typical form of such a limited area is the micro dimension channel. The series coil reactor is a kind of reactor which is composed of the coil reactor connected in series by pipes. Tubular reactor is a continuous operation reactor which appears in the middle of last century and has a large ratio of length to diameter. This kind of reactor can be very long; it can be single tube or multi tube in parallel; it can be empty tube or filled tube.

In some embodiments, the reactor may be one or more.

In some embodiments, the material of the reactor channel is monocrystalline silicon, special glass, ceramics, stainless steel or metal alloy coated with anti-corrosion coating, and polytetrafluoroethylene.

In some embodiments, the reactor modules, the reactor module groups, and the reactor module and the reactor module groups are connected in series or in parallel respectively.

In some embodiments, the continuous flow production process is carried out in a plug-and-produce integrated continuous flow reactor including six temperature zones.

In some embodiments, the oxidation condensation reaction unit of the continuous flow production process comprises four temperature zones, namely, temperature zone 1, temperature zone 2, temperature zone 3 and temperature zone 4, and the workup unit comprises two temperature zones, namely, temperature zone 5 and temperature zone 6. When the temperature of continuous temperature zone is the same, it can be regarded as the same temperature zone, for example, when the temperature of temperature zone 1 and temperature zone 2 are the same, then the integrated reactor is actually five temperature zones, temperature zone 1 (temperature zone 1+temperature zone 2), temperature zone 3, temperature zone 4, temperature zone 5 and temperature zone 6, and so on.

In some embodiments, the continuous flow production process comprises the following steps:

(a) The reaction substrate, oxidant and condensation agent are transported into the oxidation and condensation unit and pass through the temperature zone 1-4 in turn to completely react to generate the corresponding peroxycarboxylate, peroxycarbamate and peroxyketal; the reaction substrate is alcohol or alkane, and the condensation agent is alkali liquid and acyl compound when producing peroxycarboxylate and peroxycarbamate, and is acid liquid and condensation raw material, which is is alcohol or ketone when producing peroxyketal.

(b) The reaction liquid flowing out of the temperature zone 4 enters the workup unit, and then passes through the temperature zone 5 and the temperature zone 6 for workup in order to obtain the target product organic peroxide, which is selected from the peroxycarboxylate, peroxycarbamate and peroxyketal.

The organic peroxide of the target product is a product conforming to the standards of commercial industrial products. In some embodiments, the content of chloride ion in the organic peroxide of the target product is ≤0.05 wt %, and the content of other organic peroxide impurities is ≤0.1 wt %. The other organic peroxide impurities are selected from any one or more of $H_2O_2$, alkyl peroxide and dialkyl peroxide.

In some embodiments, the temperature range 1 is 0 to 100° C., preferably 0 to 80° C., more preferably 0 to 60° C., more preferably 0 to 40° C., more preferably 5 to 30° C., more preferably 5 to 20° C.

In some embodiments, the temperature of the temperature zone 2 is 10-200° C., preferably 20 to 180° C., more preferably 30 to 160° C., more preferably 40 to 130° C., more preferably 50 to 120° C., more preferably 60 to 110° C., more preferably 70 to 100° C., more preferably 80 to 90° C.

In some embodiments, the temperature range 3 is 0 to 60° C., preferably 0 to 50° C., preferably 0 to 40° C., more preferably 5 to 30° C., more preferably 5 to 20° C.

In some embodiments, the temperature of the temperature region 4 is 5 to 100° C., preferably 20 to 90° C., more preferably 30 to 80° C., more preferably 40 to 70° C., more preferably 50 to 60° C.

In some embodiments, the temperature range 5 is 0 to 60° C., preferably 0 to 50° C., preferably 0 to 40° C., more preferably 5 to 30° C., more preferably 5 to 20° C.

In some embodiments, the temperature of the temperature region 6 is 0 to 60° C., preferably 0 to 50° C., preferably 0 to 40° C., more preferably 5 to 30° C., more preferably 5 to 20° C.

It should be noted that there will be a deviation of ±3° C. in the temperature zone of actual production (including laboratory, pilot test and actual production process).

In some embodiments, the reaction substrate in step (a) is preferably from tert-butanol, tert-amyl alcohol, isopropyl benzene, 1,4-diisopropylbenzene, p-mengane, pinane, tetrahydronaphthalene, 2,4,4-trimethyl-2-pentanol, 1,3-diisopropylbenzene, dihydroxy-1,4-diisopropylbenzene, dihydroxy-1,3-diisopropylbenzene.

In some embodiments, the reaction bottom flow rate is 0.2 to 10 L/h, preferably 0.5 to 8 L/h, more preferably 1 to 6 L/h.

In some embodiments, the acid in step (a) is selected from all known organic and inorganic acids, preferably sulfuric acid, acetic acid or hydrochloric acid.

In some embodiments, the mass concentration of the acid solution is 50% to 90%, preferably 60% to 80%, more preferably 70% to 80%.

In some embodiments, the acid flow rate is 0.2 to 5 L/h, preferably 0.4 to 4 L/h, more preferably 0.5 to 3 L/h.

In some embodiments, the alkali in step (a) is selected from water-soluble metal hydroxide, water-soluble quaternary ammonium hydroxide, water-soluble tertiary amine, water-soluble metal carbonate or water-soluble metal phosphate, preferably alkali metal hydroxide, alkali earth metal hydroxide or water-soluble metal carbonate, more preferably sodium hydroxide, potassium hydroxide, sodium carbonate, potassium carbonate or lithium hydroxide.

In some embodiments, the mass concentration of the alkali liquor is 5% to 45%, preferably 15% to 35%, more preferably 20% to 30%.

In some embodiments, the flow rate of the alkali liquor is 0.2 to 10 L/h, preferably 0.3 to 9 L/h, more preferably 0.5 to 8 L/h.

In some embodiments, the acyl compounds in the condensation agent in step (a) are selected from acetyl chloride, propionyl chloride, butyryl chloride, isobutyryl chloride, valeryl chloride, 2-methylbutyryl chloride, neopentyl chloride, 2-methylvaleryl chloride, 2-ethylbutyryl chloride, 2-ethylhexyl chloride, nonyl chloride, 2,4,4-trimethylvaleryl chloride, 3,5,5-trimethylhexyl chloride, neodecanoyl chloride, decanoyl chloride, lauroyl chloride, benzoyl chloride, 2-methylbenzoyl chloride, 4-methylbenzoyl chloride, 4-chlorobenzoyl chloride, 2,4-dichlorobenzoyl chloride, naphthoyl chloride, methyl chloroformate, ethyl chloroformate, n-propyl chloroformate, isopropyl chloroformate, n-butyl chloroformate, sec-butyl chloroformate, 2-ethylhexyl chloroformate, isotridecyl chloroformate, stearyl chloroformate, cyclohexyl chloroformate, 4-tert-butyl chloroformate cyclohexyl ester, benzyl chloroformate and 2-phenoxyethyl chloroformate; the alcohol in the condensation agent is selected from tert-butanol and tert-amyl alcohol; the ketone in the condensation agent is selected from cyclohexanone, 3,3,5-trimethylcyclohexanone and methyl ethyl ketone.

In some embodiments, the flow rate of the acyl compound or condensation raw material is 0.2 to 8 L/h, preferably 0.3 to 6 L/h, more preferably 0.5 to 4 L/h.

In some embodiments, the molar ratio of acid to reaction substrate is 0.3:1 to 1.5:1, preferably 0.4:1 to 1.2:1, more preferably 0.5:1 to 1:1.

In some embodiments, the molar ratio of oxidant and reaction substrate is 0.8:1 to 2.2:1, preferably 0.9:1 to 2.1:1, more preferably 1:1 to 2:1, more preferably 1.3:1 to 1.8:1.

In some embodiments, the molar ratio of alkali to reaction substrate is 0.7:1 to 2:1, preferably 0.9:1 to 1.8:1, more preferably 1:1 to 1.6:1, more preferably 1:1 to 1.4:1.

In some embodiments, the molar ratio of acyl compound and reaction substrate is 0.5:1 to 1.2:1, preferably 0.6:1 to 1.1:1, more preferably 0.7:1 to 1:1.

In some embodiments, the molar ratio of condensation raw material and reaction substrate is 0.5:1 to 1.2:1, preferably 0.6:1 to 1.1:1, more preferably 0.7:1 to 1:1.

In some embodiments, the oxidant is selected from hydrogen peroxide and oxygen.

In some embodiments, the target product of the online continuous flow production process is tert-butyl peroxyneodecanoate, the reaction substrate is tert-butanol, the acyl compound is neodecanoyl chloride, and the oxidant is hydrogen peroxide, wherein, preferably:

The temperature of the temperature zone 1 is preferably 5 to 70° C., more preferably 5 to 60° C., more preferably 5 to 40° C., more preferably 5 to 30° C., more preferably 5 to 20° C.

The temperature of the temperature zone 2 is 30 to 160° C., more preferably 40 to 130° C., more preferably 50 to 120° C., more preferably 60 to 110° C., more preferably 70 to 100° C., more preferably 80 to 90° C.

The temperature of the temperature zone 3 is 0 to 40° C., more preferably 5 to 30° C., more preferably 5 to 20° C.

The temperature of the temperature zone 4 is 20 to 90° C., more preferably 30 to 80° C., more preferably 40 to 70° C., more preferably 50 to 60° C.

The temperature of the temperature zone 5 is 0 to 50° C., preferably 0 to 40° C., more preferably 5 to 30° C., more preferably 5 to 20° C.

The temperature of the temperature zone 6 is 0 to 50° C., preferably 0 to 40° C., more preferably 5 to 30° C., more preferably 5 to 20° C.

The production time of the production process is ≤10 min, preferably, the production time is 3 to 9 min; more preferably, the production time is 4 to 8 min; more preferably, the production time is 5 to 7 min.

The yield of tert-butyl peroxyneodecanoate is ≥68%; preferably, the yield of tert-butyl peroxyneodecanoate is ≥81%.

The content of tert-butyl peroxyneodecanoate ≥87%; preferably, the content of tert-butyl peroxyneodecanoate ≥91%.

The content of chloride ion in tert-butyl peroxyneodecanoate of the target product is 0.03 to 0.05 wt %, the content of other organic peroxide impurities is 0.05 to 0.08 wt %, and the other organic peroxide impurities are $H_2O_2$ and ditert-butyl peroxides.

The workup temperature is 0 to 50° C., preferably 0 to 40° C., more preferably 5 to 30° C., more preferably 5 to 20° C.

The flow rate of tert-butanol is 1 to 8 L/h, preferably 1.5 to 6 L/h, more preferably 2 to 4 L/h.

The acid flow rate is 0.4 to 5 L/h, preferably 0.5 to 4 L/h, more preferably 1 to 3 L/h, more preferably 1.5 to 2.5 L/h.

The flow rate of the alkali liquor is 0.4 to 9 L/h, preferably 0.8 to 7 L/h, more preferably 1 to 6 L/h, more preferably 1.2 to 5 L/h, more preferably 1.5 to 3 L/h.

The flow rate of the new decanoyl chloride is 0.4 to 7 L/h, preferably 0.8 to 6 l/h, more preferably 1 to 5 L/h, more preferably 1.5 to 4 L/h, more preferably 2 to 3 L/h.

The molar ratio of the acid and tert-butanol is 0.3:1 to 1.3:1, preferably 0.4:1 to 1.2:1, more preferably 0.5:1 to 1:1, more preferably 0.5:1 to 0.8:1.

The molar ratio of the hydrogen peroxide and tert-butanol is 0.8:1 to 1.5:1, preferably 0.9:1 to 1.4:1, more preferably 1:1 to 1.3:1, more preferably 1.05:1 to 1.2:1.

The molar ratio of the alkali and tert-butanol is 0.9:1 to 1.6:1, preferably 1:1 to 1.4:1, more preferably 1.2:1 to 1.3:1.

The molar ratio of the new decanoyl chloride and tert-butanol is 0.5:1 to 1.1:1, preferably 0.6:1 to 1:1, more preferably 0.7:1 to 0.9:1.

The mass concentration of the hydrogen peroxide is 30% to 50%.

The alkali is selected from water-soluble metal hydroxide, water-soluble quaternary ammonium hydroxide, water-soluble tertiary amine, water-soluble metal carbonate or water-soluble metal phosphate, preferably alkaline metal hydroxide, alkaline earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

In some embodiments, when the target product of the online continuous flow production process is peroxidized neodecanoic acid-1,1,3,3-tetramethyl butyl ester, the reaction substrate is 2,4,4-trimethyl-2-pentanol, the acyl compound is neodecanoyl chloride, and the oxidant is hydrogen peroxide, wherein, preferably:

The temperature of the temperature zone 1 is preferably 5 to 70° C., more preferably 5 to 60° C., more preferably 5 to 40° C., more preferably 5 to 30° C., more preferably 5 to 20° C.

The temperature of the temperature zone 2 is 30 to 160° C., more preferably 40 to 130° C., more preferably 50 to 120° C., more preferably 60 to 110° C., more preferably 70 to 100° C., more preferably 80 to 90° C.

The temperature of the temperature zone 3 is 0 to 40° C., more preferably 5 to 30° C., more preferably 5 to 20° C.

The temperature of the temperature zone 4 is 20 to 90° C., more preferably 30 to 80° C., more preferably 40 to 70° C., more preferably 50 to 60° C.

The temperature of the temperature zone 5 is 0 to 50° C., preferably 0 to 40° C., more preferably 5 to 30° C., more preferably 5 to 20° C.

The temperature of the temperature zone 6 is 0 to 50° C., preferably 0 to 40° C., more preferably 5 to 30° C., more preferably 5 to 20° C.

The production time of the production process is ≤10 min, preferably, the production time is 3 to 9 min; more preferably, the production time is 4 to 8 min; more preferably, the production time is 5 to 7 min.

The yield of neodecanoic acid-1,1,3,3-tetramethyl butyl peroxide is ≥65%; preferably, the yield of neodecanoic acid-1,1,3,3-tetramethyl butyl peroxide is ≥70%.

The content of neodecanoic acid-1,1,3,3-tetramethyl butyl peroxide is ≥80%; preferably, the content of neodecanoic acid-1,1,3,3-tetramethyl butyl peroxide is ≥90%.

The content of chloride ion in neodecanoic acid-1,1,3,3-tetramethyl butyl peroxide of the target product is 0.03 to 0.05 wt %, the content of other organic peroxide impurities is 0.05 to 0.1 wt %, and the other organic peroxide impurities are $H_2O_2$.

The mass concentration of the hydrogen peroxide is 30% to 50%.

The flow rate of the 2,4,4-trimethyl-2-pentanol is 1 to 8 L/h, preferably 1.5 to 6 L/h, more preferably 2 to 4 L/h.

The acid flow rate is 0.4 to 5 L/h, preferably 0.5 to 4 L/h, more preferably 1 to 3 L/h, more preferably 1.5 to 2.5 L/h.

The flow rate of the alkali liquor is 0.4 to 11 L/h, preferably 0.8 to 7 L/h, more preferably 1 to 6 L/h, more preferably 1.2 to 5 L/h, more preferably 1.5 to 3 L/h.

The flow rate of the new decanoyl chloride is 0.4 to 7 L/h, preferably 0.8 to 6 L/h, more preferably 1 to 5 L/h, more preferably 1.5 to 4 L/h, more preferably 2 to 3 L/h.

The molar ratio of the acid to 2,4,4-trimethyl-2-pentanol is 0.3:1 to 1.3:1, preferably 0.4:1 to 1.2:1, more preferably 0.5:1 to 1:1, more preferably 0.5:1 to 0.8:1.

The molar ratio of the hydrogen peroxide and 2,4,4-trimethyl-2-pentanol is 0.8:1 to 1.5:1, preferably 0.9:1 to 1.4:1, more preferably 1:1 to 1.3:1, more preferably 1.05:1 to 1.2:1.

The molar ratio of the base and 2,4,4-trimethyl-2-pentanol is 0.9:1 to 1.6:1, preferably 1:1 to 1.4:1, more preferably 1.2:1 to 1.3:1.

The molar ratio of the neodecanoyl chloride and 2,4,4-trimethyl-2-pentanol is 0.7:1 to 1.1:1, preferably 0.8:1 to 1:1, more preferably 0.8:1 to 0.95:1.

The alkali is selected from water-soluble metal hydroxide, water-soluble quaternary ammonium hydroxide, water-soluble tertiary amine, water-soluble metal carbonate or water-soluble metal phosphate, preferably alkaline metal hydroxide, alkaline earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

The target product of the online continuous flow production process is tert-butyl peroxide 2-ethylhexyl carbonate, the reaction substrate is tert-butanol, the acyl compound is 2-ethylhexyl chloroformate, and the oxidant is hydrogen peroxide, wherein, preferably:

The temperature of the temperature zone 1 is preferably 5 to 70° C., more preferably 5 to 60° C., more preferably 5 to 40° C., more preferably 5 to 30° C., more preferably 5 to 20° C.

The temperature of the temperature zone 2 is 30 to 160° C., more preferably 40 to 130° C., more preferably 50 to 120° C., more preferably 60 to 110° C., more preferably 70 to 100° C., more preferably 80 to 90° C.

The temperature of the temperature zone 3 is 0 to 40° C., more preferably 5 to 30° C., more preferably 5 to 20° C.

The temperature of the temperature zone 4 is 10 to 90° C., more preferably 20 to 80° C., more preferably 30 to 70° C., more preferably 40 to 60° C.

The temperature of the temperature zone 5 is 0 to 50° C., preferably 0 to 40° C., more preferably 5 to 30° C., more preferably 5 to 20° C.

The temperature of the temperature zone 6 is 0 to 50° C., preferably 0 to 40° C., more preferably 5 to 30° C., more preferably 5 to 20° C.

The production time of the production process is ≤10 min, preferably, the production time is 3 to 9 min; more preferably, the production time is 4 to 8 min; more preferably, the production time is 5 to 7 min.

The mass concentration of the hydrogen peroxide is 30% to 50%.

The yield of the 2-ethylhexylcarbonate tert-butyl peroxide is ≥70%; preferably, the yield of the 2-ethylhexylcarbonate tert-butyl peroxide is ≥81%.

The content of the 2-ethylhexylcarbonate tert-butyl peroxide is ≥95%; preferably, the content of the 2-ethylhexylcarbonate tert-butyl peroxide is ≥97%.

The content of chloride ion in the target product tert-butyl peroxide is 0.03 to 0.05 wt %, the content of other organic peroxide impurities is 0.05 to 0.08 wt %, and the other organic peroxide impurities are $H_2O_2$ and di tert-butyl peroxide.

The flow rate of tert-butanol is 1 to 8 L/h, preferably 1.5 to 6 L/h, more preferably 2 to 4 L/h.

The acid flow rate is 0.4 to 5 L/h, preferably 0.5 to 4 L/h, more preferably 1 to 3 L/h, more preferably 1.5 to 2.5 L/h.

The flow rate of the alkali liquor is 0.4 to 9 L/h, preferably 0.8 to 7 L/h, more preferably 1 to 6 L/h, more preferably 1.2 to 5 L/h, more preferably 1.5 to 3 L/h.

The flow rate of 2-ethylhexyl chloroformate is 0.4 to 7 L/h, preferably 0.8 to 6 L/h, more preferably 1 to 5 L/h, more preferably 1.5 to 4 L/h, more preferably 2 to 3 L/h.

The molar ratio of the acid and tert-butanol is 0.3:1 to 1.3:1, preferably 0.4:1 to 1.2:1, more preferably 0.5:1 to 1:1, more preferably 0.5:1 to 0.8:1.

The molar ratio of the hydrogen peroxide and tert-butanol is 0.8:1 to 1.5:1, preferably 0.9:1 to 1.4:1, more preferably 1:1 to 1.3:1, more preferably 1.05:1 to 1.2:1.

The molar ratio of the alkali and tert-butanol is 0.9:1 to 1.6:1, preferably 1:1 to 1.4:1, more preferably 1.2:1 to 1.3:1.

The molar ratio of 2-ethylhexyl chloroformate and tert-butanol is 0.5:1 to 1.1:1, preferably 0.6:1 to 1:1, more preferably 0.7:1 to 0.9:1.

The alkali is selected from water-soluble metal hydroxide, water-soluble quaternary ammonium hydroxide, water-soluble tertiary amine, water-soluble metal carbonate or water-soluble metal phosphate, preferably alkali metal hydroxide, alkali earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

In some embodiments, the target product of the online continuous flow production process is isopropyl peroxyneodecanoate, the reaction substrate is isopropyl benzene, the acyl compound is neodecanoyl chloride, and the oxidant is oxygen, wherein, preferably:

The temperature of the temperature zone 1 is preferably 0 to 80° C., more preferably 10 to 70° C., more preferably 20 to 60° C., more preferably 30 to 40° C.

The temperature of the temperature zone 2 is preferably 20 to 180° C., more preferably 30 to 150° C., more preferably 40 to 130° C., more preferably 50 to 120° C., more preferably 60 to 110° C., more preferably 70 to 100° C., more preferably 80 to 90° C.

The temperature of the temperature zone 3 is preferably 0 to 50° C., preferably 0 to 40° C., more preferably 5 to 30° C., more preferably 5 to 20° C.

The temperature of the temperature region 4 is preferably 10 to 100° C., more preferably 20 to 80° C., more preferably 30 to 60° C., more preferably 40 to 50° C.

The temperature of the temperature zone 5 is preferably 0 to 50° C., preferably 0 to 40° C., more preferably 5 to 30° C., more preferably 5 to 20° C.

The temperature of the temperature zone 6 is preferably 0 to 50° C., preferably 0 to 40° C., more preferably 5 to 30° C., more preferably 5 to 20° C.

The production time of the production process is ≤10 min, preferably, the production time is 3 to 9 min; more preferably, the production time is 4 to 8 min; more preferably, the production time is 5 to 7 min.

The yield of the isopropyl neodecanoate peroxide is ≥79%; preferably, the yield of the isopropyl neodecanoate peroxide is ≥81%.

The content of the isopropyl peroxyneodecanoate is ≥89%; preferably, the content of the isopropyl peroxyneodecanoate is ≥94%.

The content of chloride ion in the target product isopropyl neodecanoate is 0.03 to 0.05 wt %, the content of other organic peroxide impurities is 0.05 to 0.1 wt %, and the other peroxide impurities are diisopropylbenzene hydroperoxides.

The flow rate of the cumene is 0.2 to 8 L/h, preferably 0.5 to 6 L/h, more preferably 1.5 to 4 L/h, more preferably 2 to 3 L/h.

The flow rate of the alkali liquor is 0.4 to 9 L/h, preferably 0.8 to 7 L/h, more preferably 1 to 6 L/h, more preferably 1.2 to 5 L/h, more preferably 1.5 to 3 L/h.

The flow rate of the new decanoyl chloride is 0.4 to 7 L/h, preferably 0.8 to 6 l/h, more preferably 1 to 5 L/h, more preferably 1.5 to 4 L/h, more preferably 2 to 3 L/h.

The molar ratio of the oxygen and cumene is 0.8:1 to 2.2:1, preferably 1.3:1 to 2.1:1, more preferably 1.5:1 to 2:1.

The molar ratio of the alkali and cumene is 1:1 to 1.8:1, preferably 1.2:1 to 1.6:1, more preferably 1.3:1 to 1.5:1.

The molar ratio of the new decanoyl chloride and cumene is 0.5:1 to 1.1:1, preferably 0.6:1 to 1:1, more preferably 0.7:1 to 0.9:1.

The alkali is selected from water-soluble metal hydroxide, water-soluble quaternary ammonium hydroxide, water-soluble tertiary amine, water-soluble metal carbonate or water-soluble metal phosphate, preferably alkali metal hydroxide, alkali earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

In some embodiments, the target product of the online continuous flow production process is tert-butyl peroxide isopropyl carbonate, the reaction substrate is tert-butanol, the acyl compound is isopropyl chloroformate, and the oxidant is hydrogen peroxide, wherein, preferably:

The temperature of the temperature zone 1 is preferably 5 to 70° C., more preferably 5 to 60° C., more preferably 5 to 40° C., more preferably 5 to 30° C., more preferably 5 to 20° C.

The temperature of the temperature zone 2 is 30 to 160° C., more preferably 40 to 130° C., more preferably 50 to 120° C., more preferably 60 to 110° C., more preferably 70 to 100° C., more preferably 80 to 90° C.

The temperature of the temperature zone 3 is 0 to 40° C., more preferably 5 to 30° C., more preferably 5 to 20° C.

The temperature of the temperature zone 4 is 20 to 90° C., more preferably 30 to 80° C., more preferably 40 to 70° C., more preferably 50 to 60° C.

The temperature of the temperature zone 5 is 0 to 50° C., preferably 0 to 40° C., more preferably 5 to 30° C., more preferably 5 to 20° C.

The temperature of the temperature zone 6 is 0 to 50° C., preferably 0 to 40° C., more preferably 5 to 30° C., more preferably 5 to 20° C.

The production time of the production process is ≤10 min, preferably, the production time is 3 to 9 min; more preferably, the production time is 4 to 8 min; more preferably, the production time is 5 to 7 min.

The yield of the tert-butyl peroxide isopropyl carbonate is ≥70.5%; preferably, the yield of the tert-butyl peroxide isopropyl carbonate is ≥80%.

The content of tert-butyl peroxide isopropyl carbonate is ≥95%; preferably, the content of tert-butyl peroxide isopropyl carbonate is ≥97%.

The content of chloride ion in the target product is 0.03 to 0.05 wt. %, the content of other organic peroxide impurities is 0.05 to 0.08 wt. %, and the other organic peroxide impurities are $H_2O_2$ and ditert-butyl peroxide.

The flow rate of tert-butanol is 1 to 8 L/h, preferably 1.5 to 6 L/h, more preferably 2 to 4 L/h.

The acid flow rate is 0.4 to 5 L/h, preferably 0.5 to 4 L/h, more preferably 1 to 3 L/h, more preferably 1.5 to 2.5 L/h.

The flow rate of the alkali liquor is 0.4 to 9 L/h, preferably 0.8 to 7 L/h, more preferably 1 to 6 L/h, more preferably 1.2 to 5 L/h, more preferably 1.5 to 3 L/h.

The flow rate of isopropyl chloroformate is 0.4 to 7 L/h, preferably 0.8 to 6 L/h, more preferably 1 to 5 L/h, more preferably 1.5 to 4 L/h, more preferably 2 to 3 L/h.

The molar ratio of the acid and tert-butanol is 0.3:1 to 1.3:1, preferably 0.4:1 to 1.2:1, more preferably 0.5:1 to 1:1, more preferably 0.5:1 to 0.8:1.

The molar ratio of the hydrogen peroxide and tert-butanol is 0.8:1 to 1.5:1, preferably 0.9:1 to 1.4:1, more preferably 1:1 to 1.3:1, more preferably 1.05:1 to 1.2:1.

The molar ratio of the alkali and tert-butanol is 0.9:1 to 1.6:1, preferably 1:1 to 1.4:1, more preferably 1.2:1 to 1.3:1.

The molar ratio of isopropyl chloroformate and tert-butanol is 0.5:1 to 1.1:1, preferably 0.6:1 to 1:1, more preferably 0.7:1 to 0.9:1.

The mass concentration of the hydrogen peroxide is 30% to 50%.

The alkali is selected from water-soluble metal hydroxide, water-soluble quaternary ammonium hydroxide, water-soluble tertiary amine, water-soluble metal carbonate or water-soluble metal phosphate, preferably alkaline metal hydroxide, alkaline earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

In some embodiments, the target product of the online continuous flow production process is tert-amyl peroxide 2-ethylhexyl carbonate, the reaction substrate is tert-amyl alcohol, the acyl compound is chloroformic acid-2-ethylhexyl ester, and the oxidant is hydrogen peroxide The temperature of the temperature zone 1 is preferably 5 to 70° C., more preferably 5 to 60° C., more preferably 5 to 40° C., more preferably 5 to 30° C., more preferably 5 to 20° C.

The temperature of the temperature zone 2 is 30 to 160° C., more preferably 40 to 130° C., more preferably 50 to 120° C., more preferably 60 to 110° C., more preferably 70 to 100° C., more preferably 80 to 90° C.

The temperature of the temperature zone 3 is 0 to 40° C., more preferably 5 to 30° C., more preferably 5 to 20° C.

The temperature of the temperature zone 4 is 20 to 90° C., more preferably 30 to 80° C., more preferably 40 to 70° C., more preferably 50 to 60° C.

The temperature of the temperature zone 5 is 0 to 50° C., preferably 0 to 40° C., more preferably 5 to 30° C., more preferably 5 to 20° C.

The temperature of the temperature zone 6 is 0 to 50° C., preferably 0 to 40° C., more preferably 5 to 30° C., more preferably 5 to 20° C.

The production time of the production process is ≤10 min, preferably, the production time is 3 to 9 min; more preferably, the production time is 4 to 8 min; more preferably, the production time is 5 to 7 min.

The yield of the 2-ethylhexyl carbonate tert-amyl peroxide is ≥70%; preferably, the yield of the 2-ethylhexyl carbonate tert-amyl peroxide is ≥81%.

The content of the 2-ethylhexyl carbonate tert-amyl peroxide ≥95%; preferably, the content of the 2-ethylhexyl carbonate tert-amyl peroxide ≥97%.

The content of chloride ion in the target product tert-amyl peroxide is 0.03 to 0.05 wt %, the content of other organic peroxide impurities is 0.05 to 0.08 wt %, and the other organic peroxide impurities are $H_2O_2$ and tert-amyl peroxide.

The flow rate of tert-amyl alcohol is 1 to 8 L/h, preferably 1.5 to 6 L/h, more preferably 2 to 4 L/h.

The acid flow rate is 0.4 to 5 L/h, preferably 0.5 to 4 L/h, more preferably 1 to 3 L/h, more preferably 1.5 to 2.5 L/h.

The flow rate of the alkali liquor is 0.4 to 9 L/h, preferably 0.8 to 7 L/h, more preferably 1 to 6 L/h, more preferably 1.2 to 5 L/h, more preferably 1.5 to 3 L/h.

The flow rate of 2-ethylhexyl chloroformate is 0.4 to 7 L/h, preferably 0.8 to 6 L/h, more preferably 1 to 5 L/h, more preferably 1.5 to 4 L/h, more preferably 2 to 3 L/h.

The molar ratio of the acid and tert-amyl alcohol is 0.3:1 to 1.3:1, preferably 0.4:1 to 1.2:1, more preferably 0.5:1 to 1:1, more preferably 0.5:1 to 0.8:1.

The molar ratio of the hydrogen peroxide and tert-amyl alcohol is 0.8:1 to 1.5:1, preferably 0.9:1 to 1.4:1, more preferably 1:1 to 1.3:1, more preferably 1.05:1 to 1.2:1.

The molar ratio of the alkali and tert-amyl alcohol is 0.9:1 to 1.6:1, preferably 1:1 to 1.4:1, more preferably 1.2:1 to 1.3:1.

The molar ratio of 2-ethylhexyl chloroformate and tert-amyl alcohol is 0.5:1 to 1.1:1, preferably 0.6:1 to 1:1, more preferably 0.7:1 to 0.9:1.

The mass concentration of the hydrogen peroxide is 30% to 50%.

The alkali is selected from water-soluble metal hydroxide, water-soluble quaternary ammonium hydroxide, water-soluble tertiary amine, water-soluble metal carbonate or water-soluble metal phosphate, preferably alkaline metal hydroxide, alkaline earth metal hydroxide or water-soluble metal carbonate, more preferably sodium hydroxide, potassium hydroxide, sodium carbonate, potassium carbonate or lithium hydroxide.

The acid is selected from all known organic and inorganic acids, preferably sulfuric acid, phosphoric acid or trifluoroacetic acid.

It should be noted that the reaction substrate, oxidant and condensation agent used in actual production (including laboratory, pilot test and actual production process) have a deviation of ±2 percentage points in mass concentration, a deviation of ±3° C. in temperature zone and a deviation of ±5 S in production time.

The disclosure provides a scheme for producing organic peroxides by reaction substrate directly and continuously, that is, a variety of reactants are continuously input into the reactor, and the reaction products are continuously collected. With the help of the optimization of temperature zone division and temperature setting of functional units and the cooperation of functional units, the reaction can be fully realized in a short time, and the total reaction time can be shortened to 15 minutes, which greatly improves the efficiency of the process.

In the continuous flow process, the stability and reliability are good, so the product quality is stable and the reproducibility is good; the process has no amplification effect, which also solves the problem of amplification effect in the industrialization of organic peroxide continuous flow process; at the same time, the integrated continuous flow reactor has the advantages of small volume and small floor area, which greatly saves the plant land.

The second object of the disclosure is to provide a plug-and-produce integrated continuous flow reactor dedicated to any form of online continuous flow production process as described above. The integrated continuous flow reactor adopts a unit structure, including an oxidation condensation unit and a workup unit, wherein the oxidation condensation unit is used to realize the reaction substrate, oxidant and condensation. The agent reacts to generate peroxycarboxylate, peroxycarbamate and peroxyketal. The workup unit is used for the purification and cleaning of the organic peroxide. The organic peroxide is selected from peroxycarboxylate, peroxycarbamate and peroxyketal.

The third object of the disclosure is to provide a plug-and-produce integrated continuous flow reactor dedicated to any form of online continuous flow production process as mentioned above. The integrated continuous flow reactor adopts a unit structure, each unit independently comprises more than one reactor module or reactor module group, wherein the reactor module group is composed of multiple anti reactor modules. The reactor module is composed of series or parallel connection, and each unit is connected in series with each other.

The fourth object of the disclosure is to provide a plug-and-produce integrated continuous flow reactor dedicated to any form of online continuous flow production process as mentioned above. The integrated continuous flow reactor adopts a unit structure, each unit includes at least one temperature zone, each temperature zone independently includes more than one reactor module or reactor module group. The reactor module group is composed of multiple reactor modules in series or in parallel, and each temperature zone is connected in series with each other.

The above three continuous flow reactors may have more embodiments.

In some embodiments, the buffer vessel is further included between the units. The buffer is a container with a certain volume, which is mainly used to buffer the pressure fluctuation and balance the flow difference of the system, so as to make the system work more smoothly.

In some embodiments, the number of the feed ports of the integrated continuous flow reactor is one or more, and the number of the discharge ports of the integrated continuous flow reactor is one or more.

In some embodiments, the reactor module is any reactor capable of realizing continuous flow process, and the reactor is any one or any multiple of microreactor, tandem loop reactor and tubular reactor. The micro reactor, also known as micro structure reactor or micro channel reactor, is a kind of equipment in which chemical reaction takes place in a limited area with a general lateral dimension of 1 mm or less. The most typical form of such a limited area is the micro dimension channel. The series coil reactor is a kind of reactor which is composed of the coil reactor connected in series by pipes. Tubular reactor is a continuous operation reactor which appears in the middle of last century and has a large ratio of length to diameter. This kind of reactor can be very long; it can be single tube or multi tube in parallel; it can be empty tube or filled tube.

In some embodiments, the reactor may be one or more.

In some embodiments, the material of the reactor channel is monocrystalline silicon, special glass, ceramics, stainless steel or metal alloy coated with anti-corrosion coating, and polytetrafluoroethylene.

In some embodiments, the reactor modules, the reactor module groups, and the reactor module and the reactor module groups are connected in series or in parallel respectively.

In some embodiments, the integrated continuous flow reactor comprises 6 temperature zones.

In some embodiments, the oxidation condensation reaction unit of the integrated continuous flow reactor comprises four temperature zones, namely, temperature zone 1, temperature zone 2, temperature zone 3 and temperature zone 4, and the workup unit comprises two temperature zones, namely, temperature zone 5 and temperature zone 6.

In some embodiments, the temperature range 1 is 0 to 100° C., preferably 0 to 80° C., more preferably 0 to 60° C., more preferably 0 to 40° C., more preferably 5 to 30° C., more preferably 5 to 20° C.

In some embodiments, the temperature of the temperature zone 2 is 10 to 200° C., preferably 20 to 180° C., more preferably 30 to 160° C., more preferably 40 to 130° C., more preferably 50 to 120° C., more preferably 60 to 110° C., more preferably 70 to 100° C., more preferably 80 to 90° C.

In some embodiments, the temperature range 3 is 0 to 60° C., preferably 0 to 50° C., preferably 0 to 40° C., more preferably 5 to 30° C., more preferably 5 to 20° C.

In some embodiments, the temperature of the temperature region 4 is 5 to 100° C., preferably 20 to 90° C., more preferably 30 to 80° C., more preferably 40 to 70° C., more preferably 50 to 60° C.

In some embodiments, the temperature range 5 is 0 to 60° C., preferably 0 to 50° C., preferably 0 to 40° C., more preferably 5 to 30° C., more preferably 5 to 20° C.

In some embodiments, the temperature of the temperature region 6 is 0 to 60° C., preferably 0 to 50° C., preferably 0 to 40° C., more preferably 5 to 30° C., more preferably 5 to 20° C.

The fifth object of the disclosure is to provide a chemical production process, which includes the online continuous flow production process for preparing organic peroxides directly from alcohols or alkanes, and one or more subsequent production processes. For example, the chemical production process can be a polymerization process. The organic peroxide produced by the online continuous flow production process of the disclosure is used as the initiator of the polymerization process, and the process of the disclosure is seamlessly connected with the polymerization reaction process, which can form a continuity of production and use of the organic peroxide, overturning the existing production storage transportation storage use production mode, Realize the new production mode of production as use.

The sixth object of the disclosure is to provide a chemical production equipment, which comprises a plug-and-produce integrated continuous flow reactor of any form of online continuous flow production process and one or more subsequent production equipment. For example, the chemical production equipment can be a polymer production equipment. The plug-and-produce integrated continuous flow reactor of the disclosure can be directly and seamlessly connected with the polymerizer, can form a continuous production equipment for the production and use of organic peroxides, overturn the existing production storage transport storage use production mode, and realize a new production mode of production and use.

Compared with the prior art, the disclosure has the following beneficial effects:

1. Through the advantages of integrated reaction process and plug-and-produce type integrated continuous flow reactor, the disclosure thoroughly improves the process of producing organic peroxides in the prior art. For the first time, it realizes the direct production of high-risk organic peroxides from safe initiators (alcohols or alkanes), and there is no accumulation, purification and retention of dangerous alkyl peroxides (intermediate products) in the macroscopic view The standing process avoids the purification, storage and transportation steps of alkyl peroxides, realizes the online manufacturing of organic peroxides, and realizes the production and use of products at the same time. The production mode of seamless connection and synchronous linkage with downstream processes and equipment is realized, so as to realize the flexible manufacturing mode of produce-to-use and ready-to-use. That is to say, we need to produce at any time without standing. We need to produce zero stock on demand and produce on demand, and then we can stop when we meet the demand. It not only ensures the high-quality and efficient production of organic peroxides, but also seamlessly connects with the downstream process and synchronously linkage, thus avoiding the storage and transportation steps of the target product organic peroxides, fundamentally solving the cost and safety problems of cold-chain storage and transportation of alkyl peroxides and final products (peroxycarboxylates, peroxycarbamates, peroxyketals).

2. The production process of the disclosure is completely different from that of the prior art. Through only one step reaction, the reaction process and the workup process are integrated into a complete set of production process, and the products that meet the standards of commercial industrial products are directly produced in a short time (within 15 minutes), achieving high quality and high efficiency production.

3. The production process of the disclosure has strong universality. Through the organic integration of the reaction process and the reactor, the existing defects that the production process of different organic peroxides cannot be used universally are broken. By adjusting different process parameters and reactor parameters, the production of different organic peroxides can be realized on the same plug-and-produce integrated continuous flow reactor, which meets the requirements. The various demands of users improve the production efficiency.

4. The production process of the disclosure is safe and efficient, the yield and content of the organic peroxide product are high, the production cost is greatly reduced, the safety of the organic peroxide production and the downstream product production is improved, and the high efficiency, high quality and large-scale production of the organic peroxide are realized.

5. The disclosure solves the problem of industrial scale-up of organic peroxide continuous flow process. The production process of the disclosure has no scale-up effect, which greatly reduces the difficulty of industrial application. In the process of industrial scale-up, it can scale up to the required production scale at once without the tedious and complex progressively step-by-step scale-up and the adjustment and optimization of process conditions and parameters. This greatly saves manpower, material resource and project development time.

6. The safety of the production process of the disclosure has been greatly improved. The continuous flow reactor has relatively small liquid holding capacity and excellent heat transfer characteristics, and the short reaction time (within 15 minutes) makes the process safer. The liquid holding capacity of the reactor refers to the total volume of reaction materials stored in the reactor at any time when the operation reaches the steady state.

7. Compared with the prior art, the reaction time of the disclosure is greatly shortened, the reaction time is shortened by 95%, and the reaction efficiency is greatly improved.

8. In the integrated continuous flow reactor, due to the stable flow rate and production process, the product quality is stable, and the reproducibility is good.

9. The integrated continuous flow reactor has small volume and small floor area, which greatly saves the plant land.

DETAILED DESCRIPTION OF THE DISCLOSURE

The following examples, illustrating the disclosure further, are not to be constructed as being limitations thereon. It will be appreciated that all kinds of improvements, modifications and alternatives based on the disclosure by person skilled in the art after reading the descriptions of the disclosure, which are all equivalents of the disclosure, do not depart from the broad inventive concept thereof.

The following abbreviations are used in the example:
TBA: tert-butyl alcohol
TAA: tertiary amyl alcohol
NDCl: neodecanoyl chloride
2-EHCF: 2-ethylhexyl chloroformate
CYC: cyclohexanone
CBO: benzoyl chloride
Cumene: cumene
NSC904: 2,4,4-trimethyl-2-pentanol
PVCL: pivaloyl chloride
2-CHC: 2-ethylhexyl chloride
IBCL: isobutyric chloride
U535: heptanyl chloride
INCL: 3,5,5-trimethylhexyl chloride
335TCYC: 3,3,5-trimethylcyclohexanone
MEK: methyl ethyl ketone
IPCF: isopropyl chloroformate
ACL: acetyl chloride The concentrations in the examples of the disclosure are all mass concentrations. The content of the target product is measured by the effective oxygen content titration (iodometry), the chloride ion content is detected by the ion detector, and other organic peroxides are detected by the high performance liquid chromatography (HPLC). The chloride ion content in the target product of the disclosure is 0.03-0.05%, and other organic peroxides are 0.05-0.1% His organic peroxide impurities are selected from any one or more of $H_2O_2$, alkyl peroxide and dialky peroxide. There is no need to delay the pipeline in the reactor.

It should be noted that the reaction substrate, oxidant and condensation agent used in actual production (including laboratory, pilot test and actual production process) have a deviation of ±2 percentage points in mass concentration, a deviation of ±3° C. in temperature zone and a deviation of ±5 s in production time.

Examples 1-12 are the Preparation of Tert-Butyl Peroxyneodecanoate

Figure 1:
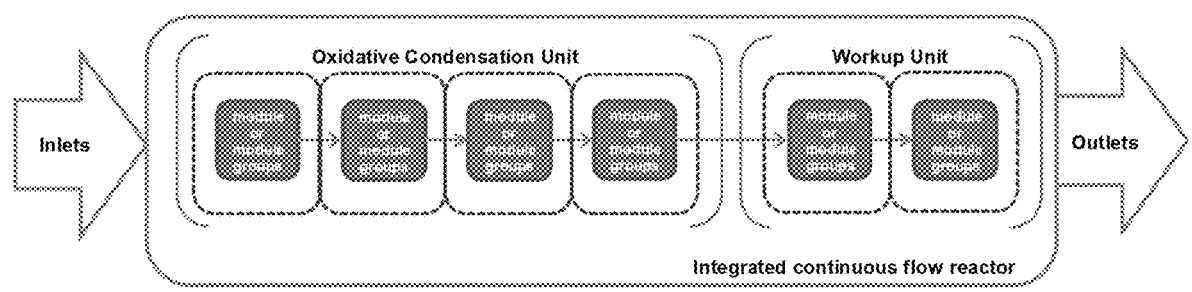
FIG. 1 is a diagram of the continuous production process according to the disclosure.
Figure 2:
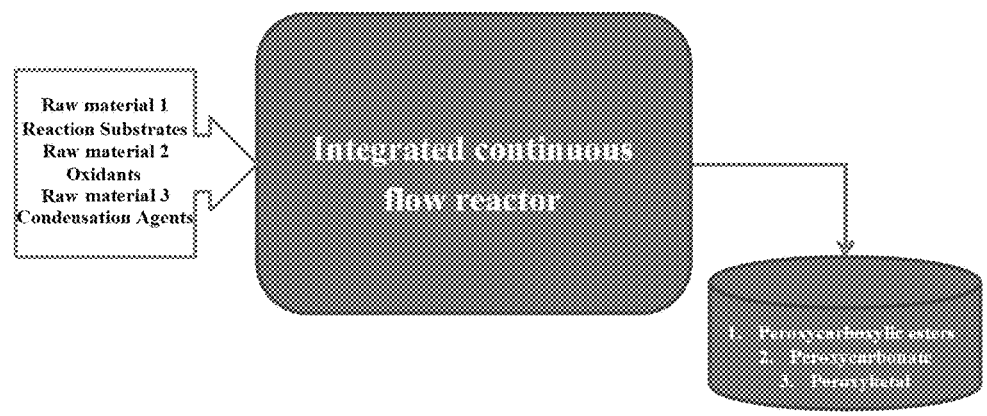
FIG. 2 is a schematic diagram of the integrated reactor according to the disclosure.

As shown in FIG. 1 and FIG. 2, the raw material 1 (sulfuric acid solution), raw material 2 (reaction substrate), raw material 3 (hydrogen peroxide solution), raw material 4 (alkali solution) and raw material 5 (acyl compound) are successively transported to the continuous reactor by constant flow pump, and then successively enter the temperature zone 1 to temperature zone 4, and the reaction is completed; the outflow temperature zone 4 reaction solution enters the temperature zone 5 and temperature zone 6 for workup to obtain pure products. Among them, feed rate 1 represents feed rate of raw material 1, feed rate 2 represents feed rate of raw material 2, feed rate 3 represents feed rate of raw material 3, feed rate 4 represents feed rate of raw material 4, and feed rate 5 represents feed rate of raw material 5.

| Examples | | Example 1 | Example 2 | Example 3 | Example 4 | Example 5 | Example 6 |
| --- | --- | --- | --- | --- | --- | --- | --- |
| Feed rate 1 | Property | $H_2SO_4/H_2O$ | $H_2SO_4/H_2O$ | $H_2SO_4/H_2O$ | $H_2SO_4/H_2O$ | $H_2SO_4/H_2O$ | $H_2SO_4/H_2O$ |
| | weight % | 70 | 70 | 70 | 60 | 80 | 70 |
| | L/h | 2.56 | 1.83 | 1.28 | 2.66 | 1.12 | 1.28 |
| Feed rate 2 | Property | $TBA/H_2O$ | $TBA/H_2O$ | $TBA/H_2O$ | $TBA/H_2O$ | $TBA/H_2O$ | $TBA/H_2O$ |
| | weight % | 94.3 | 94.3 | 94.3 | 94.3 | 94.3 | 94.3 |
| | L/h | 5.2 | 2.6 | 2.6 | 2.6 | 2.6 | 2.6 |
| Feed rate 3 | Property | $H_2O_2/H_2O$ | $H_2O_2/H_2O$ | $H_2O_2/H_2O$ | $H_2O_2/H_2O$ | $H_2O_2/H_2O$ | $H_2O_2/H_2O$ |
| | weight % | 50 | 50 | 30 | 50 | 50 | 30 |
| | L/h | 3.7 | 1.54 | 2.3 | 1.23 | 1.54 | 2.3 |

-continued

| | | | | | | | |
|---|---|---|---|---|---|---|---|
| Feed rate 4 | Property | KOH/H$_2$O | KOH/H$_2$O | KOH/H$_2$O | KOH/H$_2$O | KOH/H$_2$O | KOH/H$_2$O |
| | weight % | 20 | 5 | 20 | 45 | 30 | 35 |
| | L/h | 8 | 20.4 | 4.0 | 2.27 | 3.4 | 4.0 |
| Feed rate 5 | Property | NDCl | NDCl | NDCl | NDCl | NDCl | NDCl |
| | weight % | 98 | 98 | 98 | 98 | 98 | 98 |
| | L/h | 5.26 | 2.63 | 2.63 | 2.63 | 2.63 | 2.63 |
| Total feed | L/h | 24.72 | 29 | 12.81 | 10.63 | 11.35 | 12.81 |
| Temperature zone 1 | °C. | 70 | 60 | 40 | 30 | 20 | 5 |
| Temperature zone 2 | °C. | 160 | 130 | 120 | 110 | 100 | 90 |
| Temperature zone 3 | °C. | 40 | 30 | 20 | 5 | 0 | 30 |
| Temperature zone 4 | °C. | 90 | 80 | 70 | 60 | 50 | 40 |
| Temperature zone 5 | °C. | 50 | 40 | 30 | 20 | 5 | 0 |
| Temperature zone 6 | °C. | 50 | 40 | 30 | 20 | 5 | 0 |
| TBA:H$_2$SO$_4$:H$_2$O$_2$:KOH:NDCL mole ratio | | 1:0.5:1.2:1.2:0.7 | 1:0.8:1:1.2:0.7 | 1:0.6:0.9:1.2:0.7 | 1:1:0.8:1.2:0.7 | 1:0.6:1:1.2:0.7 | 1:0.6:0.9:1.2:0.7 |
| Production time | min | 3.3 | 3.0 | 6.0 | 6.7 | 6.64 | 6.0 |
| Total yield | % | 73.5 | 71.5 | 70 | 68.5 | 81.5 | 73 |
| Content | % | 91.5 | 90.3 | 90.4 | 90.6 | 89.4 | 90.4 |

| Examples | | Example 7 | Example 8 | Example 9 | Example 10 | Example 11 | Example 12 |
|---|---|---|---|---|---|---|---|
| Feed rate 1 | Property | H$_2$SO$_4$/H$_2$O | H$_2$SO$_4$/H$_2$O | H$_2$SO$_4$/H$_2$O | H$_2$SO$_4$/H$_2$O | H$_2$SO$_4$/H$_2$O | H$_2$SO$_4$/H$_2$O |
| | weight % | 70 | 50 | 70 | 90 | 70 | 70 |
| | L/h | 2.74 | 1.77 | 1.28 | 0.72 | 1.28 | 38.4 |
| Feed rate 2 | Property | TBA/H$_2$O | TBA/H$_2$O | TBA/H$_2$O | TBA/H$_2$O | TBA/H$_2$O | TBA/H$_2$O |
| | weight % | 94.3 | 94.3 | 94.3 | 94.3 | 94.3 | 94.3 |
| | L/h | 2.6 | 2 | 2.6 | 1.87 | 2.6 | 78 |
| Feed rate 3 | Property | H$_2$O$_2$/H$_2$O | H$_2$O$_2$/H$_2$O | H$_2$O$_2$/H$_2$O | H$_2$O$_2$/H$_2$O | H$_2$O$_2$/H$_2$O | H$_2$O$_2$/H$_2$O |
| | weight % | 50 | 50 | 50 | 50 | 30 | 30 |
| | L/h | 1.54 | 1.19 | 1.54 | 1.17 | 2.57 | 77.1 |
| Feed rate 4 | Property | KOH/H$_2$O | KOH/H$_2$O | KOH/H$_2$O | KOH/H$_2$O | KOH/H$_2$O | KOH/H$_2$O |
| | weight % | 15 | 20 | 20 | 20 | 20 | 20 |
| | L/h | 6.8 | 13.06 | 4.3 | 3.3 | 5.3 | 159 |
| Feed rate 5 | Property | NDCl | NDCl | NDCl | NDCl | NDCl | NDCl |
| | weight % | 98 | 98 | 98 | 98 | 98 | 98 |
| | L/h | 2.1 | 2.7 | 2.63 | 1.89 | 3.33 | 99.9 |
| Total feed | L/h | 15.78 | 9.84 | 12.35 | 8.4 | 12.75 | 382.5 |
| Temperature zone 1 | °C. | 5 | 5 | 5 | 5 | 5 | 5 |
| Temperature zone 2 | °C. | 80 | 70 | 60 | 50 | 40 | 40 |
| Temperature zone 3 | °C. | 20 | 20 | 5 | 20 | 5 | 5 |
| Temperature zone 4 | °C. | 30 | 20 | 50 | 60 | 60 | 60 |
| Temperature zone 5 | °C. | 5 | 5 | 30 | 5 | 20 | 20 |
| Temperature zone 6 | °C. | 5 | 5 | 5 | 5 | 5 | 5 |
| TBA:H$_2$SO$_4$:H$_2$O$_2$:KOH:NDCL mole ratio | | 1:1.3:1:1.2:0.6 | 1:0.5:1.5:0.9:1.1 | 1:0.5:1:1.3:0.7 | 1:0.3:1.05:1.4:0.5 | 1:0.6:1:1.6:0.9 | 1:0.6:1:1.6:0.9 |
| Production time | Min | 5.0 | 8.0 | 6.31 | 9.0 | 6.12 | 6.12 |
| Total yield | % | 68.6 | 80.3 | 79.7 | 71.3 | 80 | 80 |
| Content | % | 89.6 | 89.3 | 88.4 | 88.1 | 87.9 | 87.9 |

Example 13-14 are the Preparation of Tert-Amyl Peroxybenzoate

Operation method of example 1 to 12 is adopted.

| Example | | Example 13 | Example 14 |
|---|---|---|---|
| Feed rate 1 | Property | CF$_3$COOH/H$_2$O | H$_2$SO$_4$/H$_2$O |
| | weight % | 70 | 70 |
| | L/h | 1.72 | 1.6 |
| Feed rate 2 | Property | TAA/H$_2$O | TAA/H$_2$O |
| | weight % | 98 | 98 |
| | L/h | 2.22 | 2.02 |
| Feed rate 3 | Property | H$_2$SO$_4$/H$_2$O | H$_2$SO$_4$/H$_2$O |
| | weight % | 50 | 50 |
| | L/h | 1.28 | 1.16 |
| Feed rate 4 | Property | KOH/H$_2$O | KOH/H$_2$O |
| | weight % | 20 | 20 |
| | L/h | 3.05 | 2.78 |
| Feed rate 5 | Property | CB0 | CB0 |
| | weight % | 98 | 98 |
| | L/h | 1.79 | 1.63 |
| Total Feed | L/h | 9.7 | 9.19 |
| Temperature zone 1 | °C. | 5 | 5 |

| Example | | Example 13 | Example 14 |
|---|---|---|---|
| Temperature zone 2 | ° C. | 90 | 80 |
| Temperature zone 3 | ° C. | 40 | 30 |
| Temperature zone 4 | ° C. | 90 | 80 |
| Temperature zone 5 | ° C. | 30 | 30 |
| Temperature zone 6 | ° C. | 30 | 30 |

| Example | | Example 13 | Example 14 |
|---|---|---|---|
| TBA:$H_2SO_4$:$H_2O_2$:KOH:CBO mole ratio | | 1:0.6:1:1.2:0.7 | 1:0.6:1:1.2:0.7 |
| Production time | min | 7.0 | 8.0 |
| Total yield | % | 72.3 | 76.4 |
| Content | % | 78.8 | 79.4 |

Example 15-26 are the Preparation of Tert-Butyl Peroxide-2-Ethylhexyl Carbonate

The operation methods of examples 1 to 12 are adopted.

| Examples | | Example 15 | Example 16 | Example 17 | Example 18 | Example 19 | Example 20 |
|---|---|---|---|---|---|---|---|
| Feed rate 1 | Property | $H_2SO_4/H_2O$ | $H_2SO_4/H_2O$ | $H_2SO_4/H_2O$ | $H_2SO_4/H_2O$ | $H_2SO_4/H_2O$ | $H_2SO_4/H_2O$ |
| | weight % | 70 | 70 | 60 | 70 | 70 | 60 |
| | L/h | 3.66 | 1.5 | 1.49 | 2.1 | 1.28 | 1.49 |
| Feed rate 2 | Property | TBA/$H_2O$ | TBA/$H_2O$ | TBA/$H_2O$ | TBA/$H_2O$ | TBA/$H_2O$ | TBA/$H_2O$ |
| | weight % | 94.3 | 94.3 | 94.3 | 94.3 | 94.3 | 94.3 |
| | L/h | 5.2 | 1.72 | 2.6 | 2.0 | 2.6 | 2.6 |
| Feed rate 3 | Property | $H_2O_2/H_2O$ | $H_2O_2/H_2O$ | $H_2O_2/H_2O$ | $H_2O_2/H_2O$ | $H_2O_2/H_2O$ | $H_2O_2/H_2O$ |
| | weight % | 30 | 50 | 50 | 50 | 50 | 50 |
| | L/h | 4.12 | 0.91 | 1.54 | 1.18 | 2 | 1.54 |
| Feed rate 4 | Property | KOH/$H_2O$ | KOH/$H_2O$ | KOH/$H_2O$ | KOH/$H_2O$ | KOH/$H_2O$ | KOH/$H_2O$ |
| | weight % | 20 | 20 | 5 | 45 | 30 | 20 |
| | L/h | 8 | 2.84 | 23.46 | 3.33 | 3.4 | 4.6 |
| Feed rate 5 | Property | 2-EHCF | 2-EHCF | 2-EHCF | 2-EHCF | 2-EHCF | 2-EHCF |
| | weight % | 98 | 98 | 98 | 98 | 98 | 98 |
| | L/h | 5.3 | 1.75 | 2.65 | 2.16 | 2.65 | 2.65 |
| Total Rate | L/h | 26.28 | 8.7 | 31.74 | 8.76 | 11.93 | 12.85 |
| Temperature zone 1 | ° C. | 70 | 60 | 40 | 30 | 20 | 5 |
| Temperature zone 2 | ° C. | 160 | 130 | 120 | 110 | 100 | 90 |
| Temperature zone 3 | ° C. | 40 | 30 | 20 | 5 | 0 | 5 |
| Temperature zone 4 | ° C. | 90 | 80 | 70 | 60 | 50 | 40 |
| Temperature zone 5 | ° C. | 50 | 40 | 30 | 20 | 5 | 0 |
| Temperature zone 6 | ° C. | 50 | 40 | 30 | 20 | 5 | 0 |
| TBA:$H_2SO_4$:$H_2O_2$:KOH:2-EHCF mole ratio | | 1:0.8:0.8:1.2:0.7 | 1:1:0.9:1.3:0.7 | 1:0.5:1:1.4:0.7 | 1:1.2:1:0.9:0.9 | 1:0.5:1.3:1.2:0.7 | 1:0.5:1:1.6:0.7 |
| Production time | Min | 3.2 | 9.0 | 3.0 | 8.0 | 7.0 | 6.5 |
| Total yield | % | 81.37 | 72.5 | 71.88 | 71.38 | 71.1 | 71.88 |
| Content | % | 96.2 | 97.0 | 97.1 | 96.9 | 95.6 | 97.1 |

| Examples | | Example 21 | Example 22 | Example 23 | Example 24 | Example 25 | Example 26 |
|---|---|---|---|---|---|---|---|
| Feed rate 1 | Property | $H_2SO_4/H_2O$ | $H_2SO_4/H_2O$ | $H_2SO_4/H_2O$ | $H_2SO_4/H_2O$ | $H_2SO_4/H_2O$ | $H_2SO_4/H_2O$ |
| | weight % | 70 | 50 | 70 | 90 | 80 | 80 |
| | L/h | 1.28 | 2.24 | 1.28 | 2.1 | 1.12 | 33.6 |
| Feed rate 2 | Property | TBA/$H_2O$ | TBA/$H_2O$ | TBA/$H_2O$ | TBA/$H_2O$ | TBA/$H_2O$ | TBA/$H_2O$ |
| | weight % | 94.3 | 94.3 | 94.3 | 94.3 | 94.3 | 94.3 |
| | L/h | 2.6 | 2.0 | 2.6 | 4.2 | 2.6 | 78 |
| Feed rate 3 | Property | $H_2O_2/H_2O$ | $H_2O_2/H_2O$ | $H_2O_2/H_2O$ | $H_2O_2/H_2O$ | $H_2O_2/H_2O$ | $H_2O_2/H_2O$ |
| | weight % | 50 | 50 | 50 | 30 | 30 | 30 |
| | L/h | 2.16 | 1.77 | 1.67 | 2.48 | 1.54 | 46.2 |
| Feed rate 4 | Property | KOH/$H_2O$ | KOH/$H_2O$ | KOH/$H_2O$ | KOH/$H_2O$ | KOH/$H_2O$ | KOH/$H_2O$ |
| | weight % | 15 | 20 | 20 | 30 | 20 | 20 |
| | L/h | 6.8 | 3.08 | 6.8 | 6.47 | 4.0 | 120 |
| Feed rate 5 | Property | 2-EHCF | 2-EHCF | 2-EHCF | 2-EHCF | 2-EHCF | 2-EHCF |
| | weight % | 98 | 98 | 98 | 98 | 98 | 98 |
| | L/h | 2.65 | 2.88 | 2.78 | 3.6 | 3.46 | 103.8 |
| Total feed | L/h | 15.48 | 11.97 | 14.8 | 18.85 | 12.74 | 382.2 |
| Temperature zone 1 | ° C. | 5 | 5 | 5 | 5 | 5 | 5 |
| Temperature zone 2 | ° C. | 80 | 70 | 60 | 50 | 40 | 40 |
| Temperature zone 3 | ° C. | 5 | 5 | 5 | 5 | 5 | 5 |
| Temperature zone 4 | ° C. | 30 | 20 | 20 | 60 | 50 | 50 |

| | | | | | | | |
|---|---|---|---|---|---|---|---|
| Temperature zone 5 | ° C. | 5 | 5 | 5 | 5 | 5 | 5 |
| Temperature zone 6 | ° C. | 5 | 5 | 5 | 5 | 5 | 5 |
| TBA:$H_2SO_4$:$H_2O_2$:KOH:2-EHCF mole ratio | | 1:0.3:1.4:1.2:0.7 | 1:1.3:1.5:1.2:1.1 | 1:0.5:1.05:1.6:0.9 | 1:0.6:1:1.2:0.5 | 1:0.5:1:1.2:0.9 | 1:0.5:1:1.2:0.9 |
| Production time | min | 5.0 | 7.37 | 6.0 | 4.0 | 6.12 | 6.12 |
| Total yield | % | 81.5 | 71.5 | 81.38 | 80.38 | 70.1 | 71.1 |
| Content | % | 97.0 | 96.6 | 96.3 | 96.0 | 97.1 | 97.0 |

Example 27-28 are the Preparation of 1,1-Di (Tert-Butyl Peroxide) Cyclohexane

As shown in FIG. 1 and FIG. 2, raw material 1 (sulfur solution), raw material 2 (reaction substrate), raw material 3 (hydrogen peroxide solution), raw material 4 (acid solution) and raw material 5 (condensed raw material) are successively transported to the continuous reactor by constant flow pump, successively entering temperature zone 1 to temperature zone 4, and the reaction is complete; the reaction liquid flowing out of temperature zone 4 enters temperature zone 5 and temperature zone 6 for workup to obtain pure products. Among them, feed rate 1 represents feed rate of raw material 1, feed rate 2 represents feed rate of raw material 2, feed rate 3 represents feed rate of raw material 3, feed rate 4 represents feed rate of raw material 4, and feed rate 5 represents feed rate of raw material 5.

| Examples | | Example 27 | Example 28 |
|---|---|---|---|
| Feed rate 1 | Property | $H_2SO_4$/$H_2O$ | $H_3PO_4$/$H_2O$ |
| | weight % | 70 | 70 |
| | L/h | 1.28 | 1.26 |
| Feed rate 2 | Property | TBA/$H_2O$ | TBA/$H_2O$ |
| | weight % | 94.3 | 94.3 |
| | L/h | 2.6 | 2.6 |
| Feed rate 3 | Property | $H_2O_2$/$H_2O$ | $H_2O_2$/$H_2O$ |
| | weight % | 50 | 50 |
| | L/h | 1.54 | 1.54 |
| Feed rate 4 | Property | $H_2SO_4$/$H_2O$ | $H_2SO_4$/$H_2O$ |
| | weight % | 70 | 70 |
| | L/h | 0.57 | 0.57 |
| Feed rate 5 | Property | CYC | CYC |
| | weight % | 98 | 98 |
| | L/h | 0.66 | 0.66 |

| Examples | | Example 27 | Example 28 |
|---|---|---|---|
| Total feed | L/h | 6.65 | 6.63 |
| Temperature zone 1 | ° C. | 0 | 5 |
| Temperature zone 2 | ° C. | 90 | 80 |
| Temperature zone 3 | ° C. | 20 | 50 |
| Temperature zone 4 | ° C. | 65 | 75 |
| Temperature zone 5 | ° C. | 30 | 30 |
| Temperature zone 6 | ° C. | 30 | 30 |
| TBA:$H_2SO_4$:$H_2O_2$:$H_2SO_4$:CYC mole ratio | | 1:0.5:1:0.5:0.5 | 1:0.6:1:0.5:0.5 |
| Production time | min | 6.0 | 6.0 |
| Total yield | % | 65.4 | 67.5 |
| Content | % | 80.5 | 81.1 |

Example 29-38 are the Preparation of Isopropyl Neodecanoate Peroxide

As shown in FIG. 1 and FIG. 2, the raw material 1 (alkali solution), raw material 2 (reaction substrate), raw material 3 (oxygen), raw material 4 (alkali solution) and raw material 5 (acyl compound) are successively transported to the continuous reactor by constant flow pump, and then successively enter the temperature zone 1 to temperature zone 4, and the reaction is complete; the reaction fluid flowing out of the temperature zone 4 enters the temperature zone 5 and temperature zone 6 for workup to obtain pure products. Among them, feed rate 1 represents feed rate of raw material 1, feed rate 2 represents feed rate of raw material 2, feed rate 3 represents feed rate of raw material 3, feed rate 4 represents feed rate of raw material 4, and feed rate 5 represents feed rate of raw material 5.

| Examples | | Example 29 | Example 30 | Example 31 | Example 32 | Example 33 |
|---|---|---|---|---|---|---|
| Feed rate 1 | Property | $Na_2CO_3$/$H_2O$ | $Na_2CO_3$/$H_2O$ | $Na_2CO_3$/$H_2O$ | $Na_2CO_3$/$H_2O$ | $Na_2CO_3$/$H_2O$ |
| | weight % | 10 | 10 | 10 | 10 | 10 |
| | L/h | 0.6 | 0.64 | 0.6 | 0.6 | 0.6 |
| Feed rate 2 | Property | Cumene | Cumene | Cumene | Cumene | Cumene |
| | weight % | 100 | 100 | 100 | 100 | 100 |
| | L/h | 1.56 | 1.67 | 1.56 | 1.56 | 1.56 |
| Feed rate 3 | Property | $O_2$ | $O_2$ | $O_2$ | $O_2$ | $O_2$ |
| | weight % | 100 | 100 | 100 | 100 | 100 |
| | L/h | 0.5 | 0.57 | 0.55 | 0.38 | 0.33 |
| Feed rate 4 | Property | NaOH/$H_2O$ | NaOH/$H_2O$ | NaOH/$H_2O$ | NaOH/$H_2O$ | NaOH/$H_2O$ |
| | weight % | 20 | 20 | 20 | 45 | 30 |
| | L/h | 1.6 | 1.85 | 2 | 1.18 | 2 |
| Feed rate 5 | Property | NDCl | NDCl | NDCl | NDCl | NDCl |
| | weight % | 98 | 98 | 98 | 98 | 98 |
| | L/h | 1.6 | 2.46 | 1.38 | 1.15 | 2.16 |

-continued

| | | | | | | |
|---|---|---|---|---|---|---|
| Total feed | L/h | 5.86 | 7.19 | 6.09 | 4.88 | 6.65 |
| Temperature zone 1 | °C. | 80 | 70 | 60 | 40 | 30 |
| Temperature zone 2 | °C. | 180 | 150 | 130 | 120 | 110 |
| Temperature zone 3 | °C. | 50 | 40 | 30 | 20 | 5 |
| Temperature zone 4 | °C. | 100 | 80 | 60 | 50 | 40 |
| Temperature zone 5 | °C. | 50 | 40 | 30 | 20 | 5 |
| Temperature zone 6 | °C. | 50 | 40 | 30 | 20 | 5 |
| Cumene:$Na_2CO_3$:$O_2$:NaOH:NDCL Mole Ratio | | 1:0.5:2:1:0.7 | 1:0.5:2.1:1.3:1.1 | 1:0.5:2.2:1.5:0.6 | 1:0.6:1.5:1.6:0.5 | 1:0.6:1.3:1.8:0.9 |
| Production time | min | 8.57 | 7.0 | 8.0 | 9.0 | 8.0 |
| Total yield | % | 79.76 | 80.2 | 81.1 | 80.4 | 79.7 |
| Content | % | 89.5 | 89.2 | 89.1 | 94.2 | 89.52 |

| Examples | | Example 34 | Example 35 | Example 36 | Example 37 | Example 38 |
|---|---|---|---|---|---|---|
| Feed rate 1 | Property | $Na_2CO_3$/$H_2O$ | $Na_2CO_3$/$H_2O$ | $Na_2CO_3$/$H_2O$ | $Na_2CO_3$/$H_2O$ | $Na_2CO_3$/$H_2O$ |
| | weight % | 10 | 10 | 10 | 10 | 10 |
| | L/h | 0.6 | 1.47 | 0.6 | 1.1 | 33 |
| Feed rate 2 | Property | Cumene | Cumene | Cumene | Cumene | Cumene |
| | weight % | 100 | 100 | 100 | 100 | 100 |
| | L/h | 1.56 | 3.8 | 1.56 | 2.87 | 86.1 |
| Feed rate 3 | Property | $O_2$ | $O_2$ | $O_2$ | $O_2$ | $O_2$ |
| | weight % | 100 | 100 | 100 | 100 | 100 |
| | L/h | 0.5 | 1.23 | 0.5 | 0.92 | 27.6 |
| Feed rate 4 | Property | NaOH/$H_2O$ | NaOH/$H_2O$ | NaOH/$H_2O$ | NaOH/$H_2O$ | NaOH/$H_2O$ |
| | weight % | 15 | 20 | 5 | 20 | 20 |
| | L/h | 3.33 | 4.9 | 10 | 3.68 | 110.4 |
| Feed rate 5 | Property | NDCl | NDCl | NDCl | NDCl | NDCl |
| | weight % | 98 | 98 | 98 | 98 | 98 |
| | L/h | 2.16 | 5.29 | 2.16 | 3.97 | 119.7 |
| Total feed | L/h | 8.15 | 16.71 | 14.82 | 12.55 | 376.5 |
| Temperature zone 1 | °C. | 20 | 10 | 0 | 60 | 60 |
| Temperature zone 2 | °C. | 100 | 90 | 80 | 60 | 60 |
| Temperature zone 3 | °C. | 0 | 20 | 20 | 20 | 20 |
| Temperature zone 4 | °C. | 30 | 20 | 10 | 60 | 60 |
| Temperature zone 5 | °C. | 0 | 5 | 5 | 5 | 5 |
| Temperature zone 6 | °C. | 0 | 5 | 5 | 5 | 5 |
| Cumene:$Na_2CO_3$:$O_2$:NaOH:NDCL mole ratio | | 1:0.6:0.8:1.5:0.9 | 1:0.6:2.1:1.5:0.9 | 1:0.6:2:1.5:0.9 | 1:0.5:2:1.5:0.9 | 1:0.6:2:1.5:0.9 |
| Production time | min | 6.17 | 3.0 | 3.4 | 4.0 | 8.17 |
| Total yield | % | 80.3 | 81.0 | 80.7 | 81.2 | 81.4 |
| Content | % | 89.5 | 89.7 | 93.2 | 89.0 | 89.2 |

Example 39-50 are the Preparation of Neodecanoic Acid-1,1,3,3-Tetramethyl Butyl Peroxide Operation method of example 1 to 12 are adopted.

| Examples | | Example 39 | Example 40 | Example 41 | Example 42 | Example 43 | Example 44 |
|---|---|---|---|---|---|---|---|
| Feed rate 1 | Property | $H_2SO_4$/$H_2O$ | $H_2SO_4$/$H_2O$ | $H_2SO_4$/$H_2O$ | $H_2SO_4$/$H_2O$ | $H_2SO_4$/$H_2O$ | $H_2SO_4$/$H_2O$ |
| | weight % | 70 | 70 | 60 | 70 | 80 | 70 |
| | L/h | 0.55 | 2.57 | 1.49 | 3.06 | 1.45 | 0.55 |
| Feed rate 2 | Property | NSC904 | NSC904 | NSC904 | NSC904 | NSC904 | NSC904 |
| | weight % | 95 | 95 | 95 | 95 | 95 | 95 |
| | L/h | 3.87 | 11.34 | 4.5 | 8.9 | 4.5 | 3.87 |
| Feed rate 3 | Property | $H_2O_2$/$H_2O$ | $H_2O_2$/$H_2O$ | $H_2O_2$/$H_2O$ | $H_2O_2$/$H_2O$ | $H_2O_2$/$H_2O$ | $H_2O_2$/$H_2O$ |
| | weight % | 50 | 50 | 50 | 50 | 50 | 50 |
| | L/h | 1.32 | 3.88 | 1.54 | 4.12 | 2.22 | 1.32 |
| Feed rate 4 | Property | KOH/$H_2O$ | KOH/$H_2O$ | KOH/$H_2O$ | KOH/$H_2O$ | KOH/$H_2O$ | KOH/$H_2O$ |
| | weight % | 20 | 20 | 5 | 45 | 30 | 20 |
| | L/h | 3.44 | 10.08 | 20 | 4.52 | 4.5 | 3.44 |

-continued

| | | | | | | | |
|---|---|---|---|---|---|---|---|
| Feed rate 5 | Property | NDCl | NDCl | NDCl | NDCl | NDCl | NDCl |
| | weight % | 98 | 98 | 98 | 98 | 98 | 98 |
| | L/h | 2.26 | 6.63 | 2.63 | 5.23 | 2.63 | 2.26 |
| Total feed | L/h | 11.45 | 34.5 | 29.02 | 25.89 | 15.41 | 11.45 |
| Temperature zone 1 | °C. | 70 | 60 | 40 | 30 | 20 | 5 |
| Temperature zone 2 | °C. | 160 | 130 | 120 | 110 | 100 | 90 |
| Temperature zone 3 | °C. | 40 | 30 | 20 | 5 | 0 | 5 |
| Temperature zone 4 | °C. | 90 | 80 | 70 | 60 | 50 | 40 |
| Temperature zone 5 | °C. | 50 | 40 | 30 | 20 | 5 | 0 |
| Temperature zone 6 | °C. | 50 | 40 | 30 | 20 | 5 | 0 |
| NSC904:$H_2SO_4$:$H_2O_2$:KOH:NDCL mole ratio | | 1:0.3:1:1.2:0.9 | 1:0.8:1.1:1.2:0.7 | 1:1:1:1.2:1 | 1:1.2:1.4:1.2:0.9 | 1:1.3:1.5:1.6:0.9 | 1:0.5:1.04:1.2:0.9 |
| Production time | min | 9.0 | 3.0 | 3.6 | 4.0 | 6.67 | 9.0 |
| Total yield | % | 67.3 | 66.5 | 65.7 | 66.8 | 65.5 | 67.3 |
| Content | % | 88.9 | 90.4 | 80.1 | 90.8 | 81.3 | 88.9 |

| Examples | | Example 45 | Example 46 | Example 47 | Example 48 | Example 49 | Example 50 |
|---|---|---|---|---|---|---|---|
| Feed rate 1 | Property | $H_2SO_4$/$H_2O$ | $H_2SO_4$/$H_2O$ | $H_2SO_4$/$H_2O$ | $H_2SO_4$/$H_2O$ | $H_2SO_4$/$H_2O$ | $H_2SO_4$/$H_2O$ |
| | weight % | 70 | 50 | 70 | 90 | 70 | 70 |
| | L/h | 1.28 | 2.04 | 1.28 | 1 | 1.28 | 38.4 |
| Feed rate 2 | Property | NSC904 | NSC904 | NSC904 | NSC904 | NSC904 | NSC904 |
| | weight % | 95 | 95 | 95 | 95 | 95 | 95 |
| | L/h | 4.5 | 7.07 | 4.5 | 4.5 | 4.5 | 135 |
| Feed rate 3 | Property | $H_2O_2$/$H_2O$ | $H_2O_2$/$H_2O$ | $H_2O_2$/$H_2O$ | $H_2O_2$/$H_2O$ | $H_2O_2$/$H_2O$ | $H_2O_2$/$H_2O$ |
| | weight % | 50 | 50 | 30 | 50 | 50 | 50 |
| | L/h | 1.18 | 2.09 | 2.46 | 1.78 | 1.93 | 57.9 |
| Feed rate 4 | Property | KOH/$H_2O$ | KOH/$H_2O$ | KOH/$H_2O$ | KOH/$H_2O$ | KOH/$H_2O$ | KOH/$H_2O$ |
| | weight % | 15 | 20 | 20 | 20 | 20 | 20 |
| | L/h | 3 | 5.23 | 4 | 4.33 | 4.67 | 140.1 |
| Feed rate 5 | Property | NDCl | NDCl | NDCl | NDCl | NDCl | NDCl |
| | weight % | 98 | 98 | 98 | 98 | 98 | 98 |
| | L/h | 3.08 | 3.52 | 2.63 | 2.8 | 2.1 | 63 |
| Total feed | L/h | 13.04 | 20.7 | 14.89 | 14.41 | 14.48 | 434.4 |
| Temperature zone 1 | °C. | 5 | 5 | 5 | 5 | 5 | 5 |
| Temperature zone 2 | °C. | 80 | 70 | 60 | 50 | 40 | 40 |
| Temperature zone 3 | °C. | 5 | 5 | 5 | 5 | 5 | 5 |
| Temperature zone 4 | °C. | 30 | 20 | 20 | 60 | 50 | 50 |
| Temperature zone 5 | °C. | 5 | 5 | 5 | 5 | 5 | 5 |
| Temperature zone 6 | °C. | 5 | 5 | 5 | 5 | 5 | 5 |
| NSC904:$H_2SO_4$:$H_2O_2$:KOH:NDCL mole ratio | | 1:1:0.8:0.9:1.1 | 1:1:0.9:1:0.8 | 1:1:1:1.2:0.9 | 1:1:1.2:1.3:1 | 1:1:1.3:1.4:0.7 | 1:1:1.3:1.4:0.7 |
| Production time | min | 7.94 | 5.0 | 7.15 | 7.18 | 7.0 | 7.0 |
| Total yield | % | 70.3 | 65.8 | 65.2 | 66.2 | 68.5 | 68.5 |
| Content | % | 85.6 | 87.5 | 81.4 | 86.4 | 81.8 | 81.8 |

Example 51-62 are the Preparation of Tert-Butyl Peroxyisopropylcarbonate

The operation methods of embodiments 1 to 12 are adopted.

| Examples | | Example 51 | Example 52 | Example 53 | Example 54 | Example 55 | Example 56 |
|---|---|---|---|---|---|---|---|
| Feed rate 1 | Property | $H_2SO_4$/$H_2O$ | $H_2SO_4$/$H_2O$ | $H_2SO_4$/$H_2O$ | $H_2SO_4$/$H_2O$ | $H_2SO_4$/$H_2O$ | $H_2SO_4$/$H_2O$ |
| | weight % | 70 | 70 | 60 | 70 | 70 | 60 |
| | L/h | 3.66 | 1.5 | 1.49 | 2.1 | 1.28 | 1.49 |
| Feed rate 2 | Property | TBA/$H_2O$ | TBA/$H_2O$ | TBA/$H_2O$ | TBA/$H_2O$ | TBA/$H_2O$ | TBA/$H_2O$ |
| | weight % | 94.3 | 94.3 | 94.3 | 94.3 | 94.3 | 94.3 |
| | L/h | 5.2 | 1.72 | 2.6 | 2.0 | 2.6 | 2.6 |
| Feed rate 3 | Property | $H_2O_2$/$H_2O$ | $H_2O_2$/$H_2O$ | $H_2O_2$/$H_2O$ | $H_2O_2$/$H_2O$ | $H_2O_2$/$H_2O$ | $H_2O_2$/$H_2O$ |
| | weight % | 30 | 50 | 50 | 50 | 50 | 50 |
| | L/h | 4.12 | 0.91 | 1.54 | 1.18 | 2 | 1.54 |

| Examples | | | | | | | |
|---|---|---|---|---|---|---|---|
| Feed rate 4 | Property | KOH/$H_2O$ | KOH/$H_2O$ | KOH/$H_2O$ | KOH/$H_2O$ | KOH/$H_2O$ | KOH/$H_2O$ |
| | weight % | 20 | 20 | 5 | 45 | 30 | 20 |
| | L/h | 8 | 2.84 | 23.46 | 3.33 | 3.4 | 4.6 |
| Feed rate 5 | Property | IPCF | IPCF | IPCF | IPCF | IPCF | IPCF |
| | weight % | 98 | 98 | 98 | 98 | 98 | 98 |
| | L/h | 2.85 | 0.94 | 1.42 | 1.16 | 1.43 | 1.43 |
| Total feed | L/h | 23.83 | 7.91 | 30.51 | 9.77 | 10.71 | 11.66 |
| Temperature zone 1 | °C. | 70 | 60 | 40 | 30 | 20 | 5 |
| Temperature zone 2 | °C. | 160 | 130 | 120 | 110 | 100 | 90 |
| Temperature zone 3 | °C. | 40 | 30 | 20 | 5 | 0 | 5 |
| Temperature zone 4 | °C. | 90 | 80 | 70 | 60 | 50 | 40 |
| Temperature zone 5 | °C. | 50 | 40 | 30 | 20 | 5 | 0 |
| Temperature zone 6 | °C. | 50 | 40 | 30 | 20 | 5 | 0 |
| TBA:$H_2SO_4$:$H_2O_2$:KOH:IPCF mole ratio | | 1:0.8:0.8:1.2:0.7 | 1:1:0.9:1.3:0.7 | 1:0.5:1:1.4:0.7 | 1:1.2:1:0.9:0.9 | 1:0.5:1.3:1.2:0.7 | 1:0.5:1:1.6:0.7 |
| Production time | min | 3.2 | 9.0 | 3.0 | 8.0 | 7.0 | 6.5 |
| Total yield | % | 81.37 | 72.5 | 71.88 | 71.38 | 71.1 | 71.88 |
| Content | % | 96.2 | 97.0 | 97.1 | 96.9 | 95.6 | 97.1 |

| Examples | | Example 57 | Example 58 | Example 59 | Example 60 | Example 61 | Example 62 |
|---|---|---|---|---|---|---|---|
| Feed rate 1 | Property | $H_2SO_4$/$H_2O$ | $H_2SO_4$/$H_2O$ | $H_2SO_4$/$H_2O$ | $H_2SO_4$/$H_2O$ | $H_2SO_4$/$H_2O$ | $H_2SO_4$/$H_2O$ |
| | weight % | 70 | 50 | 70 | 90 | 80 | 80 |
| | L/h | 1.28 | 2.24 | 1.28 | 2.1 | 1.12 | 33.6 |
| Feed rate 2 | Property | TBA/$H_2O$ | TBA/$H_2O$ | TBA/$H_2O$ | TBA/$H_2O$ | TBA/$H_2O$ | TBA/$H_2O$ |
| | weight % | 94.3 | 94.3 | 94.3 | 94.3 | 94.3 | 94.3 |
| | L/h | 2.6 | 2.0 | 2.6 | 4.2 | 2.6 | 78 |
| Feed rate 3 | Property | $H_2O_2$/$H_2O$ | $H_2O_2$/$H_2O$ | $H_2O_2$/$H_2O$ | $H_2O_2$/$H_2O$ | $H_2O_2$/$H_2O$ | $H_2O_2$/$H_2O$ |
| | weight % | 50 | 50 | 50 | 30 | 30 | 30 |
| | L/h | 2.16 | 1.77 | 1.67 | 2.48 | 1.54 | 46.2 |
| Feed rate 4 | Property | KOH/$H_2O$ | KOH/$H_2O$ | KOH/$H_2O$ | KOH/$H_2O$ | KOH/$H_2O$ | KOH/$H_2O$ |
| | weight % | 15 | 20 | 20 | 30 | 20 | 20 |
| | L/h | 6.8 | 3.08 | 6.8 | 6.47 | 4.0 | 120 |
| Feed rate 5 | Property | IPCF | IPCF | IPCF | IPCF | IPCF | IPCF |
| | weight % | 98 | 98 | 98 | 98 | 98 | 98 |
| | L/h | 1.43 | 1.55 | 1.49 | 1.94 | 1.86 | 55.8 |
| Total feed | L/h | 14.27 | 10.64 | 13.84 | 17.19 | 11.12 | 333.6 |
| Temperature zone 1 | °C. | 5 | 5 | 5 | 5 | 5 | 5 |
| Temperature zone 2 | °C. | 80 | 70 | 60 | 50 | 40 | 40 |
| Temperature zone 3 | °C. | 5 | 5 | 5 | 5 | 5 | 5 |
| Temperature zone 4 | °C. | 30 | 20 | 20 | 60 | 50 | 50 |
| Temperature zone 5 | °C. | 5 | 5 | 5 | 5 | 5 | 5 |
| Temperature zone 6 | °C. | 5 | 5 | 5 | 5 | 5 | 5 |
| TBA:$H_2SO_4$:$H_2O_2$:KOH:IPCF mole ratio | | 1:0.3:1.4:1.2:0.7 | 1:1.3:1.5:1.2:1.1 | 1:0.5:1.05:1.6:0.9 | 1:0.6:1:1.2:0.5 | 1:0.5:1:1.2:0.9 | 1:0.5:1:1.2:0.9 |
| Production time | min | 5.0 | 7.37 | 6.0 | 4.0 | 6.12 | 6.12 |
| Total yield | % | 80.5 | 71.5 | 81.8 | 80.3 | 70.5 | 71.1 |
| Content | % | 97.0 | 97.6 | 96.9 | 98.0 | 98.1 | 97.9 |

Example 63-74 are the Preparation of Tert-Amyl Peroxide 2-Ethylhexyl Carbonate

The operation methods of embodiments 1 to 12 are adopted.

| Examples | | Example 63 | Example 64 | Example 65 | Example 66 | Example 67 | Example 68 |
|---|---|---|---|---|---|---|---|
| Feed rate 1 | Property | $H_2SO_4$/$H_2O$ | $H_2SO_4$/$H_2O$ | $H_2SO_4$/$H_2O$ | $H_2SO_4$/$H_2O$ | $H_2SO_4$/$H_2O$ | $H_2SO_4$/$H_2O$ |
| | weight % | 70 | 70 | 60 | 70 | 70 | 60 |
| | L/h | 3.66 | 1.5 | 1.49 | 2.1 | 1.28 | 1.49 |
| Feed rate 2 | Property | TAA | TAA | TAA | TAA | TAA | TAA |
| | weight % | 98 | 98 | 98 | 98 | 98 | 98 |
| | L/h | 5.7 | 1.89 | 2.86 | 2.2 | 2.86 | 2.86 |

-continued

| Feed rate 3 | Property | H₂O₂/H₂O | H₂O₂/H₂O | H₂O₂/H₂O | H₂O₂/H₂O | H₂O₂/H₂O | H₂O₂/H₂O |
|---|---|---|---|---|---|---|---|
| | weight % | 30 | 50 | 50 | 50 | 50 | 50 |
| | L/h | 4.12 | 0.91 | 1.54 | 1.18 | 2 | 1.54 |
| Feed rate 4 | Property | KOH/H₂O | KOH/H₂O | KOH/H₂O | KOH/H₂O | KOH/H₂O | KOH/H₂O |
| | weight % | 20 | 20 | 5 | 45 | 30 | 20 |
| | L/h | 8 | 2.84 | 23.46 | 3.33 | 3.4 | 4.6 |
| Feed rate 5 | Property | 2-EHCF | 2-EHCF | 2-EHCF | 2-EHCF | 2-EHCF | 2-EHCF |
| | weight % | 98 | 98 | 98 | 98 | 98 | 98 |
| | L/h | 5.3 | 1.75 | 2.65 | 2.16 | 2.65 | 2.65 |
| Total feed | L/h | 26.78 | 8.89 | 32 | 10.97 | 12.19 | 13.14 |
| Temperature zone 1 | °C. | 70 | 60 | 40 | 30 | 20 | 5 |
| Temperature zone 2 | °C. | 160 | 130 | 120 | 110 | 100 | 90 |
| Temperature zone 3 | °C. | 40 | 30 | 20 | 5 | 0 | 5 |
| Temperature zone 4 | °C. | 90 | 80 | 70 | 60 | 50 | 40 |
| Temperature zone 5 | °C. | 50 | 40 | 30 | 20 | 5 | 0 |
| Temperature zone 6 | °C. | 50 | 40 | 30 | 20 | 5 | 0 |
| TAA:H₂SO₄:H₂O₂:KOH:2-EHCF mole ratio | | 1:0.8:0.8:1.2:0.7 | 1:1:0.9:1.3:0.7 | 1:0.5:1:1.4:0.7 | 1:1.2:1:0.9:0.9 | 1:0.5:1.3:1.2:0.7 | 1:0.5:1:1.6:0.7 |
| Production time | min | 3.2 | 9.0 | 3.0 | 8.0 | 7.0 | 6.5 |
| Total yield | % | 81.3 | 72.5 | 71.8 | 71.3 | 71.6 | 71.88 |
| Content | % | 95.8 | 96.7 | 97.3 | 97.9 | 95.6 | 97.3 |

| Examples | | Example 69 | Example 70 | Example 71 | Example 72 | Example 73 | Example 74 |
|---|---|---|---|---|---|---|---|
| Feed rate 1 | Property | H₂SO₄/H₂O | H₂SO₄/H₂O | H₂SO₄/H₂O | H₂SO₄/H₂O | H₂SO₄/H₂O | H₂SO₄/H₂O |
| | weight % | 70 | 50 | 70 | 90 | 80 | 80 |
| | L/h | 1.28 | 2.24 | 1.28 | 2.1 | 1.12 | 33.6 |
| Feed rate 2 | Property | TAA | TAA | TAA | TAA | TAA | TAA |
| | weight % | 98 | 98 | 98 | 98 | 98 | 98 |
| | L/h | 2.86 | 2.2 | 2.86 | 4.62 | 2.86 | 85.8 |
| Feed rate 3 | Property | H₂O₂/H₂O | H₂O₂/H₂O | H₂O₂/H₂O | H₂O₂/H₂O | H₂O₂/H₂O | H₂O₂/H₂O |
| | weight % | 50 | 50 | 50 | 30 | 30 | 30 |
| | L/h | 2.16 | 1.77 | 1.67 | 2.48 | 1.54 | 46.2 |
| Feed rate 4 | Property | KOH/H₂O | KOH/H₂O | KOH/H₂O | KOH/H₂O | KOH/H₂O | KOH/H₂O |
| | weight % | 15 | 20 | 20 | 30 | 20 | 20 |
| | L/h | 6.8 | 3.08 | 6.8 | 6.47 | 4.0 | 120 |
| Feed rate 5 | Property | 2-EHCF | 2-EHCF | 2-EHCF | 2-EHCF | 2-EHCF | 2-EHCF |
| | weight % | 98 | 98 | 98 | 98 | 98 | 98 |
| | L/h | 2.65 | 2.88 | 2.78 | 3.6 | 3.46 | 103.8 |
| Total feed | L/h | 15.75 | 12.17 | 15.39 | 18.85 | 12.98 | 389.4 |
| Temperature zone 1 | °C. | 5 | 5 | 5 | 5 | 5 | 5 |
| Temperature zone 2 | °C. | 80 | 70 | 60 | 50 | 40 | 40 |
| Temperature zone 3 | °C. | 5 | 5 | 5 | 5 | 5 | 5 |
| Temperature zone 4 | °C. | 30 | 20 | 20 | 60 | 50 | 50 |
| Temperature zone 5 | °C. | 5 | 5 | 5 | 5 | 5 | 5 |
| Temperature zone 6 | °C. | 5 | 5 | 5 | 5 | 5 | 5 |
| TAA:H₂SO₄:H₂O₂:KOH::2-EHCF mole ratio | | 1:0.3:1.4:1.2:0.7 | 1:1.3:1.5:1.2:1.1 | 1:0.5:1.05:1.6:0.9 | 1:0.6:1:1.2:0.5 | 1:0.5:1:1.2:0.9 | 1:0.5:1:1.2:0.9 |
| Production time | min | 5.0 | 7.37 | 6.0 | 4.0 | 6.12 | 6.12 |
| Total yield | % | 81.5 | 71.5 | 81.8 | 80.38 | 70.8 | 71.0 |
| Content | % | 96.0 | 96.7 | 96.0 | 96.0 | 96.1 | 97.0 |

Examples 75-77 are the Preparation of Cumene Peroxide with Tert-Butyl

The operation method of embodiments 29-38 is adopted.

| Examples | | Example 75 | Example 76 | Example 77 |
|---|---|---|---|---|
| Feed rate 1 | Property | Na₂CO₃/H₂O | Na₂CO₃/H₂O | Na₂CO₃/H₂O |
| | weight % | 10 | 10 | 10 |
| | L/h | 0.6 | 0.6 | 18 |
| Feed rate 2 | Property | Cumene | Cumene | Cumene |
| | weight % | 100 | 100 | 100 |
| | L/h | 1.56 | 1.56 | 46.8 |
| Feed rate 3 | Property | O₂ | O₂ | O₂ |
| | weight % | 100 | 100 | 100 |
| | L/h | 0.5 | 0.5 | 15 |
| Feed rate 4 | Property | H₂SO₄/H₂O | H₂SO₄/H₂O | H₂SO₄/H₂O |
| | weight % | 70 | 70 | 70 |
| | L/h | 2 | 2 | 60 |

| Examples | | Example 75 | Example 76 | Example 77 |
|---|---|---|---|---|
| Feed rate 5 | Property | TBA | TBA | TBA |
| | weight % | 94.3 | 94.3 | 94.3 |
| | L/h | 2.16 | 2.16 | 64.8 |
| Total feed | L/h | 8.14 | 8.14 | 8.14 |
| Temperature zone 1 | °C. | 40 | 30 | 30 |
| Temperature zone 2 | °C. | 200 | 80 | 80 |
| Temperature zone 3 | °C. | 20 | 20 | 20 |
| Temperature zone 4 | °C. | 70 | 80 | 80 |
| Temperature zone 5 | °C. | 30 | 30 | 30 |
| Temperature zone 6 | °C. | 30 | 30 | 30 |
| TBA:H₂SO₄:H₂O₂:H₂SO₄:TBA mole ratio | | 1::0.6::1::0.5:1 | 1::0.6::1::0.5:1 | 1::0.6::1::0.5:1 |
| Production time | Min | 8.33 | 8.33 | 8.33 |
| Total yield | % | 79.76 | 81.7 | 81.0 |
| Content | % | 78.4 | 78.4 | 78.1 |

Examples 78-92

The corresponding organic peroxides of specific examples are as follows: examples 84 and 85 adopt the operation methods of examples 27-28, examples 78-83 and 86-92 adopt the operation methods of examples 1-12.

| Examples | 78 | 79 | 80 | 81 |
|---|---|---|---|---|
| Product name | tert-butyl peroxybenzoate | tert-butyl peroxyvalerate | tert-butyl peroxide 2-ethylhexanoate | tert-butyl peroxyisobutyrate |

| Examples | 82 | 83 | 84 | 85 |
|---|---|---|---|---|
| Product name | tert-butyl peroxyneoheptanate | tert-butyl 3,5,5-trimethylhexanoate peroxide | 1,1-di(tert-butyl peroxide)-3,3,5-trimethylcyclohexane | 2,2-di(tert-butyl peroxide) butane |

| Examples | 86 | 87 | 88 | 89 |
|---|---|---|---|---|
| Product name | tert-butyl peroxyacetate | tert-amyl peroxyvalerate | tert-amyl peroxyacetate | tert-amyl-2-ethylhexanoate peroxide |

| Examples | 90 | 91 | 92 |
|---|---|---|---|
| Product name | 1,1,3,3-tetramethyl butyl peroxide | 2-ethylhexanoate-1,1,3,3-tetramethylbutyl peroxide | 2-ethylhexanoate-1,1,3,3-tetramethylbutyl peroxide |

| Examples | | Example 78 | Example 79 | Example 80 | Example 81 | Example 82 |
|---|---|---|---|---|---|---|
| Feed rate 1 | Property | H₂SO₄/H₂O | H₂SO₄/H₂O | H₂SO₄/H₂O | H₂SO₄/H₂O | H₂SO₄/H₂O |
| | weight % | 70 | 70 | 80 | 70 | 50 |
| | L/h | 1.28 | 1.28 | 1.12 | 1.28 | 1.78 |
| Feed rate 2 | Property | TBA/H₂O | TBA/H₂O | TBA/H₂O | TBA/H₂O | TBA/H₂O |
| | weight % | 94.3 | 94.3 | 94.3 | 94.3 | 94.3 |
| | L/h | 2.6 | 2.6 | 2.6 | 2.6 | 2.6 |
| Feed rate 3 | Property | H₂O₂/H₂O | H₂O₂/H₂O | H₂O₂/H₂O | H₂O₂/H₂O | H₂O₂/H₂O |
| | weight % | 50 | 50 | 30 | 50 | 50 |
| | L/h | 1.54 | 1.54 | 2.54 | 1.54 | 1.54 |
| Feed rate 4 | Property | Na₂CO₃/H₂O | K₂CO₃/H₂O | LiOH/H₂O | KOH/H₂O | KOH/H₂O |
| | weight % | 20 | 20 | 15 | 20 | 20 |
| | L/h | 4.2 | 4.6 | 2.4 | 4.0 | 4.0 |
| Feed rate 5 | Property | CBO | PVCL | 2-EHC | IBCL | U535 |
| | weight % | 98 | 98 | 98 | 98 | 98 |
| | L/h | 1.51 | 1.6 | 2.15 | 1.36 | 1.98 |
| Total feed | L/h | 11.13 | 11.62 | 11.07 | 10.78 | 11.9 |
| Temperature zone 1 | °C. | 5 | 20 | 30 | 5 | 5 |
| Temperature zone 2 | °C. | 70 | 80 | 90 | 80 | 80 |
| Temperature zone 3 | °C. | 20 | 5 | 20 | 20 | 20 |
| Temperature zone 4 | °C. | 80 | 60 | 50 | 60 | 20 |
| Temperature zone 5 | °C. | 30 | 30 | 30 | 30 | 5 |
| Temperature zone 6 | °C. | 30 | 5 | 5 | 5 | 5 |
| TBA:H₂SO₄:H₂O₂:KOH:(CBO/PVCL/2-EHC/IBCL/U535) mole ratio | | 1:0.6:1.:1.2:0.9 | 1:0.6:1:1.2:0.9 | 1:0.6:1:1.2:0.9 | 1:0.6:1:1.2:0.9 | 1:0.6:1:1.2:0.9 |

-continued

| | | | | | | |
|---|---|---|---|---|---|---|
| Production time | min | 6.63 | 6.44 | 7.16 | 6.37 | 6.61 |
| Total yield | % | 69.3 | 70.5 | 73.2 | 67.8 | 71.5 |
| Content | % | 87.5 | 85.1 | 83.1 | 80.5 | 81.0 |

| Examples | | Example 83 | Example 84 | Example 85 | Example 86 | Example 87 |
|---|---|---|---|---|---|---|
| Feed rate 1 | Property | $H_2SO_4/H_2O$ | $H_2SO_4/H_2O$ | $H_2SO_4/H_2O$ | $H_2SO_4/H_2O$ | $H_2SO_4/H_2O$ |
| | weight % | 70 | 50 | 70 | 80 | 70 |
| | L/h | 1.28 | 1.78 | 1.28 | 1.12 | 0.92 |
| Feed rate 2 | Property | TBA/$H_2O$ | TBA/$H_2O$ | TBA/$H_2O$ | TBA/$H_2O$ | TAA/$H_2O$ |
| | weight % | 94.3 | 94.3 | 94.3 | 94.3 | 98 |
| | L/h | 2.6 | 2.6 | 2.6 | 2.6 | 1.16 |
| Feed rate 3 | Property | $H_2O_2/H_2O$ | $H_2O_2/H_2O$ | $H_2O_2/H_2O$ | $H_2O_2/H_2O$ | $H_2O_2/H_2O$ |
| | weight % | 50 | 50 | 50 | 30 | 50 |
| | L/h | 1.54 | 1.54 | 1.54 | 2.54 | 0.67 |
| Feed rate 4 | Property | KOH/$H_2O$ | $H_2SO_4/H_2O$ | $H_2SO_4/H_2O$ | KOH/$H_2O$ | KOH/$H_2O$ |
| | weight % | 20 | 70 | 70 | 20 | 5 |
| | L/h | 4.0 | 0.57 | 0.57 | 4.0 | 8.13 |
| Feed rate 5 | Property | INCL | 335TCYC | MEK | ACL | PVCL |
| | weight % | 98 | 98 | 98 | 98 | 98 |
| | L/h | 1.9 | 1.03 | 0.58 | 0.92 | 0.97 |
| Total feed | L/h | 11.32 | 7.52 | 6.57 | 11.24 | 11.85 |
| Temperature zone 1 | ° C. | 5 | 5 | 5 | 5 | 5 |
| Temperature zone 2 | ° C. | 85 | 85 | 75 | 85 | 85 |
| Temperature zone 3 | ° C. | 20 | 30 | 20 | 0 | 30 |
| Temperature zone 4 | ° C. | 80 | 90 | 80 | 80 | 50 |
| Temperature zone 5 | ° C. | 20 | 20 | 5 | 5 | 20 |
| Temperature zone 6 | ° C. | 5 | 5 | 5 | 5 | 5 |
| TBA:$H_2SO_4$:$H_2O_2$:KOH:$H_2SO$:(INCL/ 335TCYC/MEK/ACL) mole ratio | | 1:0.6:1:1.2::0.9 | 1:0.6:1:0.5::0.5 | 1:0.6:1:0.5::0.5 | 1:0.6:1:1.2::0.9 | 1:1:1.1:1.2::0.9 |
| Production time | min | 6.83 | 7.42 | 7.64 | 6.13 | 6.14 |
| Total yield | % | 65.3 | 64.5 | 67.5 | 70.4 | 72.5 |
| Content | % | 79.5 | 80.1 | 80.3 | 79.0 | 79.5 |

| Examples | | Example 88 | Example 89 | Example 90 | Example 91 | Example 92 |
|---|---|---|---|---|---|---|
| Feed rate 1 | Property | $H_2SO_4/H_2O$ | $H_2SO_4/H_2O$ | $H_2SO_4/H_2O$ | $H_2SO_4/H_2O$ | $H_2SO_4/H_2O$ |
| | weight % | 70 | 60 | 70 | 70 | 70 |
| | L/h | 1.76 | 2.05 | 1.28 | 1.28 | 38.4 |
| Feed rate 2 | Property | TAA/$H_2O$ | TAA/$H_2O$ | NSC904 | NSC904 | NSC904 |
| | weight % | 98 | 98 | 95 | 95 | 95 |
| | L/h | 2.22 | 2.22 | 4.5 | 4.5 | 135 |
| Feed rate 3 | Property | $H_2O_2/H_2O$ | $H_2O_2/H_2O$ | $H_2O_2/H_2O$ | $H_2O_2/H_2O$ | $H_2O_2/H_2O$ |
| | weight % | 50 | 50 | 30 | 50 | 50 |
| | L/h | 1.28 | 1.28 | 2.54 | 1.54 | 46.2 |
| Feed rate 4 | Property | KOH/$H_2O$ | KOH/$H_2O$ | KOH/$H_2O$ | KOH/$H_2O$ | KOH/$H_2O$ |
| | weight % | 35 | 20 | 20 | 20 | 20 |
| | L/h | 2.22 | 3.05 | 4 | 4 | 120 |
| Feed rate 5 | Property | ACL | 2-EHC | PVCl | 2-EHC | 2-EHC |
| | weight % | 98 | 98 | 98 | 98 | 98 |
| | L/h | 1.07 | 2.6 | 1.6 | 2.25 | 67.5 |
| Total feed | L/h | 9.38 | 11.2 | 13.92 | 13.57 | 412.5 |
| Temperature zone 1 | ° C. | 5 | 5 | 5 | 5 | 5 |
| Temperature zone 2 | ° C. | 85 | 85 | 80 | 80 | 80 |
| Temperature zone 3 | ° C. | 20 | 20 | 5 | 20 | 20 |
| Temperature zone 4 | ° C. | 80 | 70 | 40 | 50 | 50 |
| Temperature zone 5 | ° C. | 20 | 20 | 5 | 30 | 30 |
| Temperature zone 6 | ° C. | 5 | 5 | 5 | 5 | 5 |
| TAA/NSC904:$H_2SO_4$:$H_2O_2$:KOH:(PVCL/ ACL/2-EHC/PVCL) mole ratio | | 1:1:1.1:1.2:0.9 | 1:1:1.1:1.2:0.9 | 1:1:1.1:1.2:0.9 | 1:1:1.1:1.2:0.9 | 1:1:1.1:1.2:0.9 |
| Production time | min | 6.71 | 6.23 | 6.05 | 6.67 | 6.7 |
| Total yield | % | 74.5 | 73.3 | 67.3 | 67.6 | 67.4 |
| Content | % | 80.1 | 78.5 | 80.3 | 79.4 | 77.9 |

It can be seen from the above examples that the continuous production of organic peroxides of the disclosure has a huge advantage in reaction time, which is shortened from several hours or even 10 hours of the existing process to less than 10 minutes, and the overall yield and content are improved to a certain extent compared with the prior art. At the same time, it can be seen from embodiments 11 and 12, 25 and 26, 37 and 38, 49 and 50, 61 and 62, 73 and 74, 76 and 77, 91 and 92 that the yield is not changed and the production time is not increased after the scale-up, indicating that there is no amplification effect in the disclosure.

What is claimed is:

1. An online continuous flow production method for the preparation of organic peroxides direct from alcohols or alkanes, comprising:
   feeding reaction substrate, oxidant and condensation agent into inlets of an integrated continuous flow reactor; and
   obtaining an organic peroxide by oxidation condensation and workup;
   wherein the organic peroxides are selected from the group consisting of carboxylate peroxide, carbonate peroxide, and ketal peroxide;
   the reaction substrate is alcohol or alkane, and the condensation agent is alkali liquor and acyl compound during the production of carboxylate peroxide and carbamate peroxide;
   in the production of ketal peroxide, the reaction substrate is acid solution and condensation raw material, and the condensation raw material is alcohol or ketone;
   the general formula of a production process in the integrated continuous flow reactor is as follows:

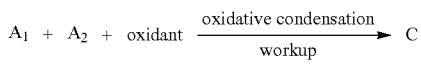

wherein, $A_1$ is alcohol or alkane; $A_2$ is selected from the group consisting of acyl chloride, chloroformate, alcohol and ketone, oxidant is selected from the group consisting of hydrogen peroxide and oxygen; C is selected from the group consisting of carboxylate peroxide, carbonate peroxide and ketal peroxide.

2. The online continuous flow production method according to claim 1, wherein
   when $A_1$ is alcohol, the general formula of $A_1$ is $R(OH)_n$, where n=an integer greater than 0;
   when $A_1$ is alkane, the general formula of $A_1$ is $R(H)_n$, where n=an integer greater than 0;
   when $A_2$ is acyl chloride, the general formula of $A_2$ is $R^1COCl$;
   when $A_2$ is chloroformate, the general formula of $A_2$ is $R^2OCOCl$;
   when $A_2$ is alcohol, the general formula of $A_2$ is $R^3(OH)_m$, where m=an integer greater than 0;
   when $A_2$ is ketone, the general formula of $A_2$ is $R^4R^{4'}(CO)$ or $R^4(CO)$ (cyclohexanone); n, m is a positive integer;
   when C is carboxylate peroxide, the general formula of C is $R(OOOCR^1)_n$, where n=an integer greater than 0;
   when C is carbonate peroxide, the general formula of C is $R(OOOCOR^2)_n$, where n=an integer greater than 0;
   when C is ketal peroxide, the general formula of C is $R^4(OOR)_2$, where n=1;
   when C is ketal peroxide, the general formula of C is $R^3(OOR)_m$, where n=1, m=an integer greater than 0;
   when C is ketal peroxide, the general formula of C is $R(OOR^3)_n$, where m=1, n=an integer greater than 0; n and m are positive integers;
   R is selected from the group consisting of saturated or unsaturated $C_1$-$C_{12}$ alkyl, unsubstituted or substituted aryl, unsubstituted or substituted heterocyclic aryl, unsubstituted or substituted saturated heterocyclic alkyl, unsubstituted or substituted partially saturated heterocyclic alkyl, unsubstituted or substituted cycloalkyl;
   $R^1$ is selected from the group consisting of saturated or unsaturated $C_1$-$C_{20}$ alkyl, unsubstituted or substituted aryl, unsubstituted or substituted heterocyclic aryl;
   $R^2$ is selected from the group consisting of saturated or unsaturated $C_1$-$C_{20}$ alkyl group, unsubstituted or substituted aryl group, unsubstituted or substituted heterocyclic aryl group, unsubstituted or substituted saturated heterocyclic alkyl group, unsubstituted or substituted partially saturated heterocyclic alkyl group, unsubstituted or substituted cycloalkyl group;
   $R^3$ is selected from the group consisting of saturated or unsaturated $C_1$-$C_{12}$ alkyl group, unsubstituted or substituted aryl group, unsubstituted or substituted heterocyclic aryl group, unsubstituted or substituted saturated heterocyclic alkyl group, unsubstituted or substituted partially saturated heterocyclic alkyl group, unsubstituted or substituted cycloalkyl group;
   $R^4$ or $R^{4'}$ is selected from the group consisting of saturated or unsaturated $C_1$-$C_{12}$ alkyl, unsubstituted or substituted aryl, unsubstituted or substituted heterocyclic aryl, unsubstituted or substituted saturated heterocyclic alkyl, unsubstituted or substituted partially saturated heterocyclic alkyl, unsubstituted or substituted cycloalkyl;
   $R(OH)_n$ is selected from the group consisting of tert-butanol, tert-amyl alcohol, 2,4,4-trimethyl-2-pentanol, 2,5-dimethyl-2,5-dihydroxyhexane, dihydroxy-1,4-diisopropylbenzene and dihydroxy-1,3-diisopropylbenzene;
   $R(H)_n$ is selected from the group consisting of cumene, 1,4-diisopropylbenzene and 1,3-diisopropylbenzene;
   $R^1COCl$ is selected from the group consisting of acetyl chloride, propionyl chloride, butyryl chloride, isobutyryl chloride, valeryl chloride, 2-methylbutyryl chloride, neopentyl chloride, 2-methylvaleryl chloride, 2-ethylbutyryl chloride, 2-ethylhexyl chloride, nonyl chloride, 2,4,4-trimethylvaleryl chloride, 3,5,5-trimethylhexyl chloride, neodecanoyl chloride, decanoyl chloride, lauroyl chloride, benzoyl chloride, 2-methylbenzoyl chloride, 4-methylbenzoyl chloride, 4-chlorobenzoyl chloride, 2,4-di chlorobenzoyl chloride, naphthyl chloride;
   $R^2OCOCl$ is selected from the group consisting of methyl chloroformate, ethyl chloroformate, n-propyl chloroformate, isopropyl chloroformate, n-butyl chloroformate, sec-butyl chloroformate, 2-ethylhexyl chloroformate, isotridecyl chloroformate, stearyl chloroformate, cyclohexyl chloroformate, 4-tert-butyl cyclohexyl chloroformate, benzyl chloroformate and 2-phenoxyethyl chloroformate;
   $R^3(OH)_n$ is selected from the group consisting of tert-butanol, tert-amyl alcohol, 2,4,4-trimethyl-2-pentanol, 2,5-dimethyl-2,5-dihydroxyhexane, dihydroxy-1,4-diisopropylbenzene and dihydroxy-1,3-diisopropylbenzene;

R$^4$R$^{4'}$(CO) is selected from the group consisting of methyl ethyl ketone; R$^4$(CO) is selected from cyclohexanone, 3,3,5-trimethylcyclohexanone.

3. The online continuous flow production method according to claim 1, wherein the organic peroxide C is selected from the group consisting of:
t-butyl peroxybenzoate CAS No.: 614-45-9, t-amyl peroxybenzoate CAS No.: 4511-39-1, t-butyl peroxyacetate CAS No.: 107-71-1, t-butyl terephentate peroxide CAS No.: 927-07-1, t-amyl terephentate peroxide CAS No.: 29240-17-3, t-butyl peroxyneodecanoate CAS No.: 26748-41-4, t-amyl peroxyneodecanoate CAS No.: 68299-16-1, t-butyl peroxide 2-ethylcaproate CAS No.: 3006-82-4, t-amyl peroxide 2-ethylcaproate CAS No.: 686-31-7, t-butyl isobutyrate peroxide CAS No.: 109-13-7, t-butyl neoheptanoate peroxide CAS No.: 26748-38-9, t-butyl 3,5,5-trimethylhexanoate peroxide CAS No.: 13122-18-4, t-butyl 2-ethylhexanoate peroxide CAS No.: 34443-12-4, t-butyl 2-ethylhexanoate peroxide t-amyl carbonate CAS No.: 70833-40-8, 1,1-di-tert-butyl peroxide-3,3,5-trimethylcyclohexane CAS No.: 6731-36-8, 1,1-di(tert-butyl peroxide) cyclohexane CAS No.: 3006-86-8, 2,2-di(tert-butyl peroxide) butane CAS No.: 2167-23-9, isopropylphenyl peroxyneodecanoate CAS No.: 26748-47-0, 1,1,3,3-tetramethylbutyl peroxyneodecanoate CAS No.: 51240-95-0 1,1,3,3-tetramethylbutyl peroxypivalate CAS No.: 22288-41-1, 1,1,3,3-tetramethyl-butyl peroxy-2-ethylhexanoate CAS No.: 22288-43-3, 1,1-bis(tert-amty peroxy) cyclohexane CAS No.: 15667-10-4, t-amyl acetate peroxide CAS No.: 690-83-5, t-butyl isopropyl carbonate peroxide CAS No.: 2372-21-6, and t-butyl peroxide isopropylbenzene CAS No.: 3457-61-2.

4. The online continuous flow production method according to claim 1, wherein the production method has no macroscopical accumulation, purification and stagnation of alkyl peroxides.

5. The online continuous flow production method according to claim 4, wherein the general formula of the alkyl peroxide is R(OOH)$_n$, wherein R is selected from the group consisting of saturated or unsaturated C$_1$-C$_{12}$ alkyl, unsubstituted or substituted aryl, unsubstituted or substituted heterocyclic aryl, unsubstituted or substituted saturated heterocyclic group, unsubstituted or substituted partially saturated heterocyclic group, and unsubstituted or substituted cyclic Alkyl, n≥1, n is a positive integer;
the alkyl peroxide is selected from the group consisting of: t-butyl hydroperoxide CAS No.: 75-91-2, t-amyl hydroperoxide CAS No.: 3425-61-4, CAS No.: 4212-43-5, 1,1,3,3-tetramethyl-butyl hydroperoxide CAS No.: 5809-08-5, cumene hydroperoxide CAS No.: 80-15-9, 2,5-dimethyl-2,5-bis (hydroperoxides) hexane CAS No.: 3025-88-5, and dihydroxy-1,4-diisopropylbenzene CAS No.: 3159-98-6.

6. The online continuous flow production method according to claim 1, wherein the content of chloride ion in the target organic peroxide is ≤0.05 wt %, the content of other organic peroxide impurities is ≤0.1 wt %, and the other organic peroxide impurities are any one or more of H$_2$O$_2$, alkyl peroxide and dialkyl peroxide.

7. The online continuous flow production method according to claim 1, wherein the production time of the method is ≤15 min.

8. The online continuous flow production method according to claim 1, wherein the yield of the organic peroxide is ≥64%.

9. The online continuous flow production method according to claim 1, wherein the content of the organic peroxide is ≥77%.

10. The online continuous flow production method according to claim 1, wherein the temperature of the oxidative condensation method is 0-200° C.

11. The online continuous flow production method according to claim 1, wherein the workup temperature is 0 to 60° C.

12. The online continuous flow production method according to claim 1, wherein the alkali is selected from the group consisting of water-soluble metal hydroxide, water-soluble quaternary ammonium hydroxide, water-soluble tertiary amine, water-soluble metal carbonate and water-soluble metal phosphate.

13. The online continuous flow production method according to claim 1, wherein the mass concentration of the alkali liquor is 5% to 45%.

14. The online continuous flow production method according to claim 1, wherein the acid is selected from the group consisting of sulfuric acid, phosphoric acid and trifluoroacetic acid.

15. The online continuous flow production method according to claim 1, wherein the mass concentration of the acid solution is 50% to 90%.

16. The online continuous flow production method according to claim 1, wherein the oxidant is hydrogen peroxide or oxygen.

17. The online continuous flow production method according to claim 1, wherein the reaction substrate is selected from the group consisting of tert-butanol, tert-amyl alcohol, isopropyl benzene, 1,4-diisopropylbenzene, p-mengane, pinane, tetrahydronaphthalene, 2,4,4-trimethyl-2-pentanol, 1,3-diisopropylbenzene, dihydroxy-1,4-diisopropylbenzene, dihydroxy-1,3-diisopropylbenzene.

18. The online continuous flow production method according to claim 1, wherein the acyl compounds in the condensation agent are selected from acetyl chloride, propionyl chloride, butyryl chloride, isobutyryl chloride, valeryl chloride, 2-methylbutyryl chloride, neopentyl chloride, 2-methylpentyl chloride, 2-ethylbutyryl chloride, 2-ethylhexyl chloride, nonyl chloride, 2,4,4-trimethylpentyl chloride, 3,5,5-trimethyl hexyl chloride, neodecanoyl chloride, decanoyl chloride, lauroyl chloride, benzoyl chloride, 2-methylbenzoyl chloride, 4-methylbenzoyl chloride, 4-chlorobenzoyl chloride, 2,4-dichlorobenzoyl chloride, naphthoyl chloride, methyl chloroformate, ethyl chloroformate, n-propyl chloroformate, isopropyl chloroformate, n-butyl chloroformate, sec-butyl chloroformate, 2-ethylhexyl chloroformate, isotridecyl chloroformate ester, stearyl chloroformate, cyclohexyl chloroformate, 4-tert-butyl cyclohexyl chloroformate, benzyl chloroformate and 2-phenoxyethyl chloroformate; the alcohol in the condensation agent is selected from the group consisting of tert-butanol and tert-amyl alcohol; the ketone in the condensation agent is selected from the group consisting of cyclohexanone, 3,3,5-trimethylcyclohexanone and methyl ethyl ketone.

19. The online continuous flow production method according to claim 1, wherein the molar ratio of acid and reaction substrate is 0.3:1 to 1.5:1.

20. The online continuous flow production method according to claim 1, wherein the molar ratio of oxidant and reaction substrate is 0.8:1 to 2.2:1.

21. The online continuous flow production method according to claim 1, wherein the molar ratio of alkali and reaction substrate is 0.7:1 to 2:1.

22. The online continuous flow production method according to claim 1, wherein the molar ratio of acyl compound and reaction substrate is 0.5:1 to 1.2:1.

23. The online continuous flow production method according to claim 1, wherein the molar ratio of the raw condensation material and the reaction substrate is 0.5:1 to 1.2:1.

* * * * *